United States Patent
Prestrelski et al.

(10) Patent No.: US 8,110,209 B2
(45) Date of Patent: Feb. 7, 2012

(54) INTRACUTANEOUS INJECTION

(75) Inventors: Steven Prestrelski, Mountain View, CA (US); Kevin Brodbeck, Palo Alto, CA (US)

(73) Assignee: Xeris Pharmaceuticals Inc., Austin, TX (US)

( * ) Notice: Subject to any disclaimer, the term of this patent is extended or adjusted under 35 U.S.C. 154(b) by 1377 days.

(21) Appl. No.: 10/539,931

(22) PCT Filed: Dec. 22, 2003

(86) PCT No.: PCT/US03/40876
§ 371 (c)(1),
(2), (4) Date: May 10, 2006

(87) PCT Pub. No.: WO2004/057959
PCT Pub. Date: Jul. 15, 2004

(65) Prior Publication Data
US 2006/0211982 A1    Sep. 21, 2006

Related U.S. Application Data

(60) Provisional application No. 60/435,466, filed on Dec. 20, 2002.

(51) Int. Cl.
*A61F 2/02* (2006.01)
(52) U.S. Cl. ...................................... 424/423
(58) Field of Classification Search ........................ None
See application file for complete search history.

(56) References Cited

U.S. PATENT DOCUMENTS

| | | |
|---|---|---|
| 3,016,895 A | 1/1962 | Sein |
| 4,927,571 A | 5/1990 | Huang et al. |
| 5,716,640 A | 2/1998 | Kamei et al. |
| 5,932,547 A | 8/1999 | Stevenson et al. |
| 5,977,082 A | 11/1999 | Gatti et al. |
| 5,981,489 A | 11/1999 | Stevenson et al. |
| 6,066,619 A | 5/2000 | Stevenson et al. |
| 6,124,261 A | 9/2000 | Stevenson et al. |
| 6,235,712 B1 | 5/2001 | Stevenson et al. |
| 6,264,990 B1 | 7/2001 | Knepp et al. |
| 6,495,164 B1 | 12/2002 | Ramstack et al. |
| 6,627,600 B2 | 9/2003 | Boutignon |
| 6,667,061 B2 | 12/2003 | Ramstack et al. |
| 6,730,328 B2 | 5/2004 | Maskiewicz et al. |
| 7,005,421 B2 | 2/2006 | Gatti et al. |
| 7,163,704 B2 | 1/2007 | Zhang |

(Continued)

FOREIGN PATENT DOCUMENTS

WO    WO 98/09613 A1    3/1998

(Continued)

OTHER PUBLICATIONS

Encyclopedia of Pharmaceutical Technology, vol. 6, Suspensions, pp. 3597-3610, 2007.*

(Continued)

*Primary Examiner* — Carlos Azpuru
(74) *Attorney, Agent, or Firm* — Kilpatrick Townsend & Stockton LLP

(57) ABSTRACT

The delivery of biopharmaceutical and other therapeutic agents parenterally to an animal via a minimally invasive, low pain administration is provided. The agents are delivered to the patient via, e.g., the epidermal, dermal, or subcutaneous layer of the skin in a concentrated form of injectable paste of slurry.

19 Claims, 7 Drawing Sheets

U.S. PATENT DOCUMENTS

| | | |
|---|---|---|
| 7,371,406 B2 | 5/2008 | Ramstack et al. |
| 7,396,841 B2 | 7/2008 | Doen et al. |
| 7,498,312 B2 | 3/2009 | Cohen et al. |
| 7,582,311 B1 | 9/2009 | Cleland et al. |
| 7,651,703 B2 | 1/2010 | Cleland et al. |
| 2001/0005781 A1 | 6/2001 | Thomas et al. |
| 2003/0003105 A1 | 1/2003 | Gerber |
| 2003/0026844 A1 | 2/2003 | Lee et al. |
| 2003/0093157 A1 | 5/2003 | Casares et al. |
| 2003/0119825 A1 | 6/2003 | Folger et al. |
| 2003/0170289 A1 | 9/2003 | Chen et al. |
| 2003/0191157 A1 | 10/2003 | Doen et al. |
| 2004/0052872 A1 | 3/2004 | Ionascu |
| 2004/0142043 A1 | 7/2004 | Maeda et al. |
| 2004/0176341 A1 | 9/2004 | Chou et al. |
| 2005/0019436 A1 | 1/2005 | Burch et al. |
| 2005/0020808 A1 | 1/2005 | Song et al. |
| 2005/0069591 A1 | 3/2005 | Bernstein et al. |
| 2005/0244514 A1 | 11/2005 | Zhang |
| 2006/0058386 A1 | 3/2006 | Gentile et al. |
| 2006/0160823 A1 | 7/2006 | Witchey-Lakshmanan et al. |
| 2006/0234995 A1 | 10/2006 | Cohen et al. |
| 2008/0096967 A1 | 4/2008 | Lopez et al. |
| 2008/0132493 A1 | 6/2008 | Folger et al. |
| 2008/0160067 A1 | 7/2008 | Boeckh et al. |
| 2008/0220069 A1 | 9/2008 | Allison |
| 2008/0305161 A1 | 12/2008 | Shah et al. |
| 2009/0176720 A1 | 7/2009 | Cohen et al. |
| 2009/0215883 A1 | 8/2009 | Bouzada et al. |
| 2010/0098735 A1 | 4/2010 | Jain et al. |

FOREIGN PATENT DOCUMENTS

| | | |
|---|---|---|
| WO | WO 98/16250 A1 | 4/1998 |
| WO | WO 98/27963 A2 | 7/1998 |
| WO | WO 00/16829 A | 3/2000 |
| WO | WO 01/78687 A1 | 10/2001 |
| WO | WO 02/00137 A1 | 1/2002 |
| WO | WO 02/49660 A1 | 6/2002 |
| WO | WO 03/007782 A2 | 1/2003 |
| WO | WO 03/041684 A2 | 5/2003 |
| WO | WO 2004/037242 A1 | 5/2004 |
| WO | WO 2004/057959 A2 | 7/2004 |
| WO | WO 2004/091666 A1 | 10/2004 |
| WO | WO 2004/098643 A2 | 11/2004 |
| WO | WO 2005/010079 A1 | 2/2005 |
| WO | WO 2006/031376 A2 | 3/2006 |
| WO | WO 2007/140312 A2 | 12/2007 |
| WO | WO 2008/030469 A2 | 3/2008 |
| WO | WO 2008/041245 A2 | 4/2008 |
| WO | WO 2009/045837 A1 | 4/2009 |
| WO | WO 2009/060473 A2 | 5/2009 |
| WO | WO 2010/018596 A2 | 2/2010 |

OTHER PUBLICATIONS

Meyer, J.D. et al., "Preparation and in Vitro Characterization of Gentamycin-Impregnated Biodegradable Beads Suitable for Treatment of Osteomyelitis," *Journal of Pharmaceutical Sciences*, Sep. 1998, vol. 87, No. 9, pp. 1149-1154.

* cited by examiner

INTRACUTANEOUS INJECTION

FIELD OF THE INVENTION

The invention relates to the delivery of biopharmaceutical and other therapeutic agents parenterally to a mammal via a minimally invasive, low pain administration. The agents are delivered to the patient via, e.g., the epidermal, dermal, or subcutaneous layer of the skin.

BACKGROUND OF THE INVENTION

Parenteral injection refers to the administration of drugs or vaccines via injection under or through one or more layers of skin or mucus membranes of an animal. Standard injections are given into the subcutaneous or intramuscular region of an animal, e.g., a human patient. These deep locations are targeted because the tissue expands more easily, relative to shallow dermal sites, to accommodate the 0.1-3.0 cc (ml) injection volumes required to deliver most therapeutic agents.

Generally, injections have been classified into different categories, including (1) solutions ready for injection; (2) dry, soluble ready to be combined with a solvent just prior to being injected into a patient; (3) dry, insoluble products ready to be combined with a suitable injection medium prior to administration; (4) suspensions ready for injection; and (5) emulsions ready for injection. Such injectable formulations are administered by routes including intravenous, subcutaneous, intradermal, intramuscular, intraspinal, intrasisternal, and intrathecal. The nature of the therapeutic agent quickly determines the route of administration. On the other hand, the desired route of administration places constraints on the therapeutic formulation itself. For example, solutions for subcutaneous administration require strict attention to tonicity adjustment in order to avoid irritation to the nerves and tissue in the surrounding area of injection. Likewise, suspensions are not administered directly into the blood stream in view of the potential of insoluble particles blocking capillaries.

In comparison to other dosage forms and routes of administration, injectables possess certain advantages, including immediate physiological action (e.g., via intravenous injection), avoidance of intestinal absorption problems attended with many drugs, and the accurate administration of the desired dose into the blood stream of a patient. On the other hand, one of the disadvantages of injectables is the pain and discomfort present at the site of administration associated with certain pharmaceutically active agents, as well as the trauma of having a needle inserted under the skin or into a vein. There is a degree of discomfort for the patient with each injection which is administered.

Currently, biopharmaceutical agents are typically reconstituted into sterile solutions and are administered into the subcutaneous or intramuscular space using a large gauge needle, e.g., in the range 18-30 gauge. Pain is caused by the depth of the penetration of the needle, the size "gauge" of the needle, the large volume of injection, and the diffusion of drug away from the site of injection, among other things. In addition to problems with administration of injectables due to pain associated with the same, there are other draw backs of current practices with respect to injections. For example, many protein and sustained release drugs require reconstitution immediately prior to administration. Dosing of drugs can be inflexible and inaccurate. Further, many formulations need to be refrigerated in order to protect the drugs from degrading hydrolysis reactions. Further, present administration systems are wasteful in that the injection device retains a significant amount of the drug product. Further, to effect delivery of the necessary dose required, an injectable formulation typically must be concentrated and stabilized. Standard injections are given in the liquid form. Products that are sold as liquids or a lyophilized powder require reconstitution in an aqueous carrier prior to injection. Many therapeutic protein and vaccine products are produced in a dry, solid form to promote stability while on the shelf. These formulations are diluted prior to injection in sterile water, phosphate buffer solution, or isotonic saline.

Unlike the subcutaneous and intramuscular regions, the dermal area is shallow with limited expansion. The stratum corneum is relatively thin—only 5 to 15 microns. The dermal area is unable to accommodate injection volumes of greater than 0.5 ml required for most therapeutic injectables. Intradermal injections have been used to date primarily for diagnostic testing to determine exposure to diseases. Certain therapeutic substances (e.g., hepatitis B vaccines) are more effectively absorbed into or react with the immune response system when injected intradermally. Other substances require intradermal administration for diagnostic testing. Intradermal tissues are well supplied with blood vessels and have a rapid rate of absorption of substances injected therein. The absorption rate and limited volume (<0.5 ml) that may be injected intradermally has rendered intradermal injections generally unsatisfactory for therapeutic purposes. The ventral surface of the forearms and the scapular surfaces are the most common used for intradermal injection. Other potential sites include the upper arms and upper chest areas.

Syringes for intradermal injections are known. A typical syringe includes a needle shaft, lumen, bevel, hilt or hub opening, barrel or cartridge which contains liquid medications, tip and a plunger which includes an activation flange at one end and a rubber stopper at an opposite end. The barrel is the outer round part, typically made of glass or plastic. The plunger, typically made of plastic, is the piston-like part that moves up and down inside the barrel. The tip is the small projection that fits inside the hub of the needle. There are two types of tips—plain and locking. A plain tip is tapered to fit tightly inside the hub of the needle and holds the needle in place by friction. A locking tip has a treaded outer collar, which is sized to accept the needle hub. The basic components of the needle are the hub, shaft and bevel. The hub is the enlarged portion at the end of the needle that fits over the tip of the syringe. The shaft is the long slender part, and the bevel is the angled tip of the needle. Syringes for administration of intradermal injection typically are 1 ml (1 cc) tuberculin, between 25-27 gauge, with a ¼ or ½ inch needle, and inject a volume of 0.1 to 0.5 ml maximum for adults. Most intradermal injections are 0.1 ml maximum. Some syringes are prepackaged with needles already attached; others are not. Therefore, the 1 ml syringe may require that the needle be attached to the syringe using aseptic technique. Once the syringe and needle have been assembled the medication is drawn up from a vial or ampule. Vials are single or multidose glass containers, which are sealed with a thick rubber stopper. The stopper or diaphragm is covered with a metal or plastic cap to ensure sterility. The medication in vials is either in the form of a solution or dry sterile powder. If the medication is in powder form, it will have to be reconstituted with the appropriate diluent in the appropriate volume. The proper procedure for drawing a drug from a vial is to remove the protective cap on the vial and clean off the diaphragm with an alcohol swab. The plunger is pulled back to aspirate the needed amount of air and the needle is inserted in the center of the rubber diaphragm. Air is injected and the drug is aspirated. Errors occur if the wrong diluent or the wrong amount of diluent is used. If the medication is in an ampule, the ampule must be opened. A filter (e.g., filter straw) is required to prevent tiny glass particles from being drawn up into the syringe. Failure to use a filter needle may result in patent injury and/or blockage of the needle preventing flow of medication. The filter must be removed and the needle attached to the syringe prior to administration. Errors occur where there is a failure to remove the filter resulting in injection of glass particles. Further, the additional step of attaching and removing the filter from the syringe requires aseptic technique to reduce the risk of nosocomial infections.

There is needed in the art methods and formulations to provide concentrated dosing of therapeutic agents, vaccines, and other biopharmaceuticals in a concentrated dose via intracutaneous injection into the epidermal, dermal or subcutaneous layer of the skin. It is further desirable to provide such formulations in a stabilized platform which does not require reconstitution or refrigeration. It is further desirable to prepare such formulations and administer the same in a manner which substantially avoids pain associated with injection of such agents.

SUMMARY OF THE INVENTION

It is an object of the present invention to provide an injectable formulation which may be administered into the epidermal, dermal or subcutaneous layer of an animal to effect pain-free or substantially pain-free administration of a therapeutic agent.

It is a further object of the present invention to provide a concentrated injectable formulation containing an effective amount of a therapeutic agent which may be injected into the epidermal, dermal or subcutaneous layer of skin of an animal.

It is a further object of the present invention to provide a device for injection of a therapeutic agent into the epidermal, dermal or subcutaneous layer of the skin of an animal which effects pain-free or substantially pain-free administration of a therapeutic agent.

It is a further object of the invention to provide a device, formulation, and method for injection of a therapeutic agent which achieves substantially 100% displacement of the dose out of the injection needle.

It is a further object of the invention to provide a method for the administration of an injectable formulation into the epidermal, dermal, or subcutaneous layer of an animal to effect pain-free or substantially pain-free administration of a therapeutic agent.

It is another object of the invention to provide a method of providing an injectable formulation for intracutaneous administration which is stable and which does not require refrigeration or reconstitution prior to use.

It is another object of the invention to provide a delivery device and formulations providing intracutaneous injections which overcome the problems and limitations of conventional devices and methods for intracutaneous injection.

It is another object of the invention to provide a delivery device, formulations and methods which minimize medication and injection technique errors.

It is another object of the invention to provide a delivery device and formulations providing intracutaneous injections which allow self-administration.

It is another object of the invention to provide a delivery device and formulations providing intracutaneous injections which allow for administration of concentrated formulations of therapeutic agents.

In accordance with the above objects and others, the present invention is related in part to a device for injection of a therapeutic agent into the epidermal, dermal or subcutaneous layer of the skin of an animal which effects pain-free or substantially pain-free administration of a therapeutic agent, comprising a needle suitable for intracutaneous injection, said needle having a lower end containing a unit dose of a therapeutic agent homogeneously contained within a slurry or paste; and a biasing device arranged at an upper end of said needle; said needle and said biasing device being contained within a housing, said housing including an activator, such that when said injection device is set against the skin of an animal, said activator can be activated to release said biasing device, thereby causing said needle to penetrate the skin of an animal and forcing substantially all of said unit dose out of a tip located at the lower end of said needle. In preferred embodiments, the needle is at least about 5 cm in length, and is from about 18 to about 31 gauge, and in certain preferred embodiments from about 27 to about 30 gauge.

In preferred embodiments, the injection device further comprises a plunger disposed against an upper end of said unit dose contained within said needle, said biasing device forcing said plunger against said formulation and forcing substantially all of said formulation out of said lower tip of said needle upon activation of said device. The plunger may comprise, e.g., a wire having a diameter slightly smaller than the inner diameter of the needle or a deformable gel disposed within the upper part of the needle.

In preferred embodiments, the injection device further comprises a retraction device contained within said housing, said retraction device being activated after the injection is made in order to retract the empty needle.

In preferred embodiments, the injection device further comprises a skin positioner attached to the lower end of said housing, said skin positioner being capable of stretching the skin of a mammal when said injection device is set against the skin of a mammal to be injected in order to: i) provide therapeutic agent into the site of injection; ii) provide for a shallow injection; and iii) to reduce pain caused by the penetration of the needle into the skin of the mammal upon activation of the injection device. The needle is preferably incorporated within the housing of the injection device such that the needle extends from said lower end of the housing only when the injection device is actuated during use.

In preferred embodiments, the lower tip of the needle has a substantially flat orientation (e.g., a beveled, close-ended or sealed end) prior to use when containing the unit dose, and configured such that a peak is created for puncturing the skin, the tip being capable of expanding as the formulation is forced through it during use, thereby allowing the formulation to flow out of the needle tip.

In certain preferred embodiments, multiple needle systems are contained within the housing, such that multiple penetrations are made to the skin during use, simultaneously dosing a larger (total) dose of the therapeutic agent while maintaining small individual volumetric injections. The greater surface exposure is useful, e.g., for the administration of vaccines (to expose a larger number of antigen-presenting cells in an area).

In certain preferred embodiments, an upper portion of the needle is widened in a smooth manner relative to the lower tip of the needle, in order to hold more volume of the therapeutic formulation. The widening of the needle is accomplished in a manner such that the slurry will flow without constriction through the needle and out of the end of needle.

The present invention is further directed to an injectable formulation for intracutaneous administration which is stable and which does not require refrigeration or reconstitution prior to use, comprising from about 0.1 to about 10 microliters of an ultraconcentrated semisolid or solid formulation comprising an effective amount of a therapeutic agent homogeneously contained within a pharmaceutically acceptable carrier, said formulation comprising from about 20% to about 85% solids, by weight, and in certain preferred embodiments from about 50% to about 80%, by weight. The therapeutic agent has a mean particle size range from 10 nanometers (0.01 microns) to about 100 microns, with no particles being larger than about 1 mm, and in certain embodiments more preferably has a mean particle size from about 0.1 microns to about 25 microns, with no particles being larger than about 50 microns, and in certain embodiments has mean particle size of the therapeutic agent from about 1 to about 10 microns.

In certain preferred embodiments, the formulation further comprises a carrier (e.g., one or more polymers) which imparts thixotropic properties to the formulation. The therapeutic agent is preferably homogeneously incorporated into the thixotropic pharmaceutically acceptable carrier, and said formulation is in the form of a paste or slurry.

In certain preferred embodiments, the therapeutic agent is homogeneously contained within a pharmaceutically acceptable carrier. The carrier is preferably biocompatible and is a non-solvent to the powder. The carrier in certain preferred embodiments fills the spaces between particles in a way that makes them flow. In certain embodiments, the carrier is selected from the group consisting of alkyl benzoates, aryl benzoates, aralkyl benzoates, triacetin, dimethyl sulfoxide (DMSO), N-methyl-2-pyrrolidone (NMP), alkanes, cyclic alkanes, chlorinated alkanes, fluorinated alkanes, perfluorinated alkanes and mixtures thereof.

In certain preferred embodiments, the injectable formulation is in controlled (slow) release form. In such embodiments, for example, the formulation may comprise a pharmaceutically acceptable polymer in an amount effective to slow the release of the therapeutic agent from said formulation upon administration via injection into the epidermal, dermal or subcutaneous layer of an animal. Additionally, or alternatively, the therapeutic agent may be incorporated into liposomes or conjugated to or incorporated with polysaccharides and/or other polymers to provide a controlled release of the therapeutic agent from said formulation upon administration via injection into the epidermal, dermal or subcutaneous layer of an animal. In certain preferred embodiments, the therapeutic agent may be incorporated into a biocompatible polymer and a biocompatible solvent having low water miscibility that forms a viscous gel with the polymer and limits water uptake by the composition. Such compositions are described in U.S. Pat. No. 6,130,200 (Brodbeck, et al.), hereby incorporated by reference in its entirety, and for example utilize a poly(lactide-co-glycolide) copolymer together with an effective plasticizing amount of a solvent comprising a lower alkyl or aralkyl ester of benzoic acid to form a gel with the polymer.

The invention is further directed in part to a method for the administration of an injectable formulation into the epidermal, dermal or subcutaneous layer of an animal to effect pain-free or substantially pain-free administration of a therapeutic agent, comprising injecting from about 0.1 to about 10 microliters of an ultraconcentrated semisolid or solid formulation (e.g., a slurry or paste) comprising from about 20 to about 85% solids, by weight and comprising an effective amount of a therapeutic agent into the epidermal, dermal or subcutaneous skin layer of an animal.

In preferred embodiments, the therapeutic agent is processed, e.g., via spray-drying or lyophilization, in order to decrease its particle size to a mean particle size suitable for injection through a narrow gauge needle (e.g., 27 to 30 gauge).

In preferred embodiments, the therapeutic agent is incorporated into a non-aqueous or semi-aqueous pharmaceutically acceptable carrier. In further preferred embodiments, the formulation exhibits thixotropic properties upon injection from an injection device.

The present invention is further directed in part to methods of treating mammals, e.g., human patients, utilizing the injectable formulations, injection devices and methods of preparation of the present invention.

For purposes of the present invention, the term "therapeutic agent" encompasses drugs, vaccines and the like used in the prevention, diagnosis, alleviation, treatment or cure of a condition, ailment or disease.

The term "intracutaneous" encompasses administration into the epidermal, dermal or subcutaneous skin layer.

The term "pharmaceutically acceptable carrier" means a pharmaceutically acceptable solvent, suspending agent or vehicle for delivering a compound of the present invention to the animal or human. The carrier may be liquid, semisolid or solid.

The term "pharmaceutically acceptable" ingredient, excipient or component is one that is suitable for use with humans and/or animals without undue adverse side effects (such as toxicity, irritation, and allergic response) commensurate with a reasonable benefit/risk ratio.

The term "therapeutic agent" means an agent that effects a desired, beneficial, often pharmacological, effect upon administration to a human or an animal, whether alone or in combination with other pharmaceutical excipients or inert ingredients.

The term "chemical stability" means that with respect to the therapeutic agent, an acceptable percentage of degradation products produced by chemical pathways such as oxidation or hydrolysis is formed. In particular, a formulation is considered chemically stable if no more than about 20% breakdown products are formed after one year of storage at the intended storage temperature of the product (e.g., room temperature); or storage of the product at 30° C./60% relative humidity for one year; or storage of the product at 40° C./75% relative humidity for one month, and preferably three months.

The term "physical stability" means that with respect to the therapeutic agent, an acceptable percentage of aggregates (e.g., dimers, trimers and larger forms) is formed. In particular, a formulation is considered physically stable if no more that about 15% aggregates are formed after one year of storage at the intended storage temperature of the product (e.g., room temperature); or storage of the product at 30° C./60% relative humidity for one year; or storage of the product at 40° C./75% relative humidity for one month, and preferably three months.

The term "stable formulation" means that at least about 65% chemically and physically stable therapeutic agent remains after two months of storage at room temperature. Particularly preferred formulations are those which retain at least about 80% chemically and physically stable therapeutic agent under these conditions. Especially preferred stable formulations are those which do not exhibit degradation after sterilizing irradiation (e.g., gamma, beta or electron beam).

The term "bioavailability" is defined for purposes of the present invention as the extent to which the therapeutic agent is absorbed from the formulation.

The term "systemic" means, with respect to delivery or administration of a beneficial agent to a subject, that beneficial agent is detectable at a biologically-significant level in the blood plasma of the subject.

The term "pastes" means a concentrate of the therapeutic agent dispersed in a pharmaceutically acceptable carrier having a thick consistency to form a viscous semisolid.

The term "slurry" means a thin paste.

The term "controlled-release" is defined for purposes of the present invention as the release of the therapeutic agent at such a rate that blood (e.g., plasma) concentrations are maintained within the therapeutic range but below toxic concentrations over a period of time of about one hour or longer, preferably 12 hours or longer.

The term "intracutaneous" means into the epidermal or dermal layer of the skin of an animal, e.g., a human.

DETAILED DESCRIPTION

Figure 1:
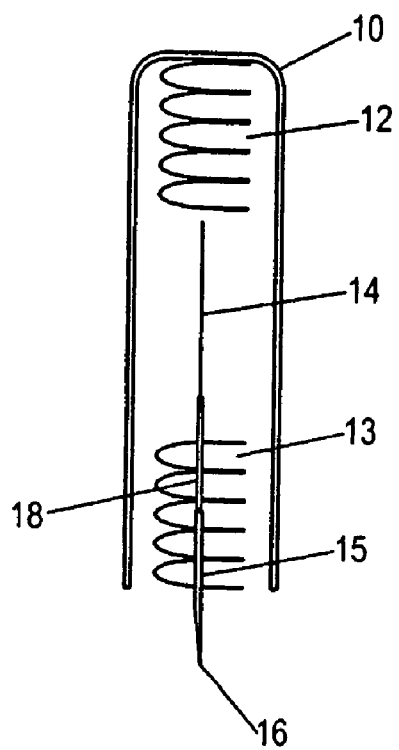
FIG. 1 is a cross-sectional view of an injection device in accordance with the present invention.

The methods, formulations and devices of the invention relate in certain preferred embodiments to the administration of a therapeutic agent into the epidermal, dermal or subcutaneous layer of an animal.

There are at least three common causes of pain associated with needle/syringe injections which are the addressed by the invention. These causes of pain vary as a result from the following variables: (i) the volume of liquid delivered to the patient in a typical liquid administration; (ii) the size (diameter, thickness) of the needle; and (iii) the depth of the injection. Low-pain or pain-free administration is accomplished by addressing each of these variables.

There are at least four alternative elements to this invention that produce the effect of a pain-free administration of a therapeutic agent into the intracutaneous space of a patient resulting in systemic circulation of the agent or exposure of an antigen to the immune system in the case of vaccines. These elements are as follows: (i) a low volume injection; (ii) a concentrated therapeutic agent (e.g., drug) particle group or dispersed solid formulation surrounded by a protective solution (typically non-aqueous); (iii) a thin walled narrow-gauge needle; and (iv) a shallow injection of the concentrated dispersion of therapeutic agent (e.g., drug slurry) into the epidermal or dermal layer of the skin. Further, the current invention addresses the speed of injection and provides an auto-injector with a hidden needle.

Formulation

Standard injection volumes associated with most therapeutic injections are too large to avoid pain in the epidermal, dermal, or subcutaneous layer. In order to accomplish a low-pain or pain-free injection (or administration) of a therapeutic agent into an animal (e.g., a human patient), therefore, a much smaller injection volume is required. Standard injections are given into the subcutaneous or intramuscular region of a patient. These deep locations are targeted because the tissue expands more easily, relative to shallow dermal sites, to accommodate the 0.1-1.0 ml injection volumes required by most therapeutic injectables. Injection of large viscous volumes tends to cause more pain than small dilute volumes. However, viscous medications have not been administered intracutaneously in the past because a large lumen needle is required. Such needles cannot be used for intracutaneous administration. Additionally, liquid formulations must be injected slowly when done intracutaneously to avoid tissue damage and volumes greater than 0.5 ml cannot be administered intracutaneously.

The injectable formulations of the present invention contain the necessary delivered dose of therapeutic agent (e.g., the dose required for drug therapy) and are preferably low volume, e.g., the injectable formulation containing a therapeutic dose of the therapeutic agent has a volume of at least about 0.01 microliters (the lower limit being a function of the filling equipment), more preferably from about 1 microliter to about 250 microliters. This is accomplished in certain preferred embodiments by concentrating the dose of therapeutic agent in a stable form in a suitable carrier for injection in accordance with the invention. In certain embodiments, the low volume of injectable dose is accomplished by concentrating the dose of therapeutic agent in a stable form within a suitable carrier.

Preferably, the low volume formulations of the present invention are administrable without being diluted, or reconstituted, or refrigerated. Therapeutic dosages of the therapeutic agent are achieved in preferred embodiments by concentrating the therapeutic agent into an injectable paste (solid) or slurry.

Standard injections are given in liquid form. Products are sold as liquids or a lyophilized powder that require reconstitution in an aqueous carrier prior to injection. Many therapeutic protein and vaccine products are produced in a solid particulate form to promote stability while on the shelf. These formulations are diluted prior to injection in sterile water, phosphate buffer solution, or isotonic saline. In contrast, in certain preferred embodiments of the present invention, the therapeutic agent is concentrated using the same particle preparation processes (e.g., spray drying, lyophilization, etc.) techniques routinely employed by the pharmaceutical industry to prepare formulations for injection. However, in accordance with the goals of the present invention, the particulate low volume formulation is injected or otherwise administered into the animal (e.g., human patient) without diluting formulation prior to injection as required by reconstitution products.

To aid in the ease of injection, the concentrated solid containing the therapeutic agent(s) is surrounded by a liquid to form a slurry or paste. The formulations of the present invention can contain a wide range of solids content, typically from about 1.0% to about 99.0% solids, and more preferably from about 20% to about 80% solids. The size of the drug formulation particulates, the solid content of the formulation, and the thickness of the needle will influence the pressure required to inject the formulation. The concentrated solid formulation is placed into the injection device and is presented in the device in such fashion that it is able to flow out of the needle upon actuation of the device in order to deliver the payload (dose of concentrated solid formulation).

Alternatively, in certain embodiments, the dose of solid particulate therapeutic agent need not be incorporated into a carrier. In such alternative embodiments, the flowability of the formulation through the needle of the injection device is imparted instead via a lubricating material that is applied to the inner surface of the needle section of the injection device (and/or any other section of the device to which the solid formulation makes surface contact) or coated onto the outside of the drug particles. Such a material may be, for example, grease or silicon oil.

The injectable formulations of the invention are advantageously prepared as a slurry or paste in certain preferred embodiments of the invention, in order to (i) reduce the pressure required for injection of solid concentrates; (ii) promote uniform delivery of the paste; and (iii) provide additional shelf stability against aggregation, oxidation and hydrolysis related degradation pathways.

In certain preferred embodiments, the slurry or paste containing the therapeutic agent preserves the therapeutic agent in a stable form for a prolonged period of time, e.g., sufficient to provide a desired shelf-life of the formulation without unacceptable levels of degradation of the therapeutic agent prior to use. A desired property of the slurry or paste is that it be non-aqueous, and non-reactive with respect to the particulate drug formulation. In such embodiments, it is possible to store the slurry or paste directly in the injection device itself. Alternatively, it will be appreciated by those skilled in the art that the particulate formulation of the therapeutic agent can be dried (e.g., freeze-dried) and stored separately from the injection device. Thereafter, prior to use, a sufficient amount of a liquid can be added to the particulate formulation of the therapeutic agent to prepare the slurry or paste (ultra concentrated semisolid), which is then introduced into the injection device. No concentration step is necessary in such embodiments.

In certain preferred embodiments, the semisolid formulation must be stabilized in order to ensure the stability of the therapeutic agent incorporated therein. The stability of the injectable formulation is achieved via the inclusion of a stabilizing agent into the slurry or paste. In other preferred embodiments, in addition to or instead of the inclusion of a stabilizing agent, a liquid, or mixture of liquid, that can enhance or maintain neutrality of the stability of the therapeutic agent can be included as a portion or all of the injectable carrier. Such stabilizing agents include, for example, surfactants, pluronics, gels, and amphoteric compounds. In certain embodiments, the therapeutic agent contained in the slurry formulation can be stabilized from undesirable degradation via the addition of materials such as triacetin, n-methyl-2-pyrrolidone, or benzyl benzoate (which may be added, e.g., just after spray-drying, etc. . . . ). Other examples of stabilizers are mineral oil, perflorodecalyn, ethyl benzoate, octane, pluronics, glycolated compounds, amino acids, polymers that form gels (e.g., PEG) polyols, oils and waxes. In certain preferred embodiments, the stabilizer is added into the (original) powder comprising the therapeutic agent prior to spray-drying or lyophilization; alternatively the stabilizer can be added to the carrier directly, as well).

In certain preferred embodiments where the therapeutic agent comprises protein or nucleic acid-containing particles, it is preferably suspended in anhydrous, aprotic, hydrophobic, non-polar vehicles of low reactivity (such as mineral oil, perfluorodecalin, methoxyflurane, perfluorotributylamine and tetradecane) to result in stable flowable non-aqueous formulations. Such formulations are described in U.S. Pat. No. 6,264,990, hereby incorporated by reference. In other preferred embodiments, the formulation can be stabilized via the inclusion of a stabilizing polyol such as described in U.S. Pat. No. 6,290,991, hereby incorporated by reference.

In certain preferred embodiments, the stabilizing agent comprises from about 1 to about 80 percent of the formulation, by weight. However, the amount of stabilizing agent (e.g., surfactant) included in the formulations of the present invention is determined by the limiting concern that the final product should provide a stable pharmaceutically acceptable formulation. Other suitable pharmaceutically acceptable stabilizing agents include acacia, benzalkonium chloride, cholesterol, emulsifying wax, glyceryl monostearate, lanolin alcohols, lecithin, poloxamer, poloxyethylene castor oil derivatives, poloxyethylene sorbitan fatty acid esters, poloxyethylene stearates, sodium lauryl sulfates, sorbitan esters, stearic acid, and triethanolamine.

Surfactants may be incorporated into the semisolid therapeutic formulation in order, e.g., to aid in the flow of the formulation through the needle of the injection device, and/or to aid in the dissolution of the solid therapeutic agent. The surfactants which may be used in the present invention generally include pharmaceutically acceptable anionic surfactants, cationic surfactants, amphoteric (amphipathic/amphophilic) surfactants, and non-ionic surfactants.

Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates, alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl beta-aminoproprionates.

Suitable pharmaceutically acceptable wetting (solubilizing) agents, include pharmaceutically acceptable non-ionic surfactants such as, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters.

In certain embodiments, preferred surfactants include, e.g., hexadecylamine, octadecyl amino acid esters, octadecylamine, lysolecithin, dimethyl-dioctadecylammonium bromide, N,N-dicoctadecyl-N'—N'bis(2-hydroxyethyl-propane diamine), methoxyhexadecylglycerol, and pluronic polyols (e.g., a desirable quantity of an alkylene polyoxide (sold by BASF under the name of Pluronic PE 4300). The particular surfactant should be chosen with respect with the therapeutic agent, keeping in mind compatibility and ability to dissolve or wet the therapeutic agent.

Similarly, any liquid that enhances the injectability of a solid through a needle should be considered a viable aspect of this invention. Thus, in certain embodiments, the slurry formulation for injection includes one or more injectability enhancing agents. Examples of such agents include, but are not limited to, silicon oil, waxes, oils, lubricants, greases, and petroleum jelly.

Suitable pharmaceutical carriers are described in Remington: The Science and Practice of Pharmacy, 19th ed., Mack Publishing Company, Easton, Pa., 1995, some of which include polymeric, natural occurring structured liquids or suspensions, or surfactant-based systems. In particular suitable carrier solutions include, but are not limited to, dextran dissolved in triacetin solution (water level 0-7%); PLGA dissolved in weak solvent (NMP, alkyl benzoate, triacetin or mixtures thereof). The term "solvent" means a pharmaceutically acceptable solvent that dissolves the viscoelastic agent.

In certain preferred embodiments, the liquid carrier for this invention is one that possesses thixotropic characteristics and a positive yield value to suspend a solid in a paste while being discharged through the needle. Yield value is a measurement of the force or pressure exerted on a liquid at rest. Newtonian fluids have a shear stress of zero as they are capable of exerting force, other than gravimetric, unless the fluid is put into motion. However, a positive yield value is not a function of a solutions thickness, though many viscoelastic solutions are viscous. It is not a solutions thickness that supports and carries particles suspended in the viscoelastic solution, but the presence of a three dimensional structure within the liquid. To sufficiently suspend particles, a solution preferably will have a yield value greater than the force gravity applied across the cross section of the solution, e.g., PLGA in triacetin has a yield value equivalent to seven times the force applied by gravity. A thixotropic solution or thick solution of suitable density will ensure homogeneous displacement of drug through the solution. Without this property, the liquid can be dispensed from the needle under force leaving the solids behind, eventually plugging the needle—an unsuccessful administration. It is also important for purposes of the present invention that the structure solution maintain its properties under flow conditions. If this is not the case, suspended particles could become unsuspended as they pass through the narrow needle causing clogging.

The formulation for injection may include other pharmaceutically acceptable ingredients for injection, including but not limited to additional pharmaceutically acceptable excipients for injection. Such additional ingredients which are included in the slurry or paste preferably possess necessary rheological properties to allow for displacement of the solids under reasonable pressures (i.e., do not interfere with the injectability of the formulation). As a general rule, thumb pressure is the lower end (e.g., a few newtons) of the pressure that can be generated with a syringe.

Such additional ingredients include e.g., antioxidizing agents, such as sodium bisulfite, sodium sulfite, ascorbic acid or methionine, either alone or combined, are suitable stabilizing agents. Also used are citric acid salts thereof, or sodium EDTA; preservatives, such as benzalkonium chloride, methyl- or propyl-paraben, or chlorobutanol, potassium sorbate, sorbic acid, sulfur dioxide, propyl gallate, the parabens, ethyl vanillin, glycerin, phenol, and parachlorophenol.

Any suitable dosage of the therapeutic agent may be administered in the methods of the present invention. The compound or salt or prodrug thereof chosen for a particular application, the carrier and the amount will vary widely depending on the species of the warm blooded animal or human, the type of cancer, or the particular viral infection being treated, and depending upon the effective inhibitory concentrations observed in trial studies. The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired.

Polymers that may be useful in the invention are preferably biodegradable and/or biocompatible and may include, but are not limited to polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, chitin, chitosan, and copolymers, terpolymers and mixtures thereof.

Presently preferred polymers are polylactides, polyglycolides, and copolymers of lactic acid and glycolic acid. These polymers may include amounts of other comonomers that do not substantially affect the advantageous results which can be achieved in accordance with the present invention. As used herein, the term "lactic acid" includes the isomers L-lactic acid, D-lactic acid, DL-lactic acid and lactide while the term "glycolic acid" includes glycolide. Most preferred are poly(lactide-co-glycolide)copolymers, commonly referred to as PLGA. The polymer may have a monomer ratio of lactic acid/glycolic acid of from about 100:0 to about 15:85, preferably from about 60:40 to about 75:25 and an especially useful copolymer has a monomer ratio of lactic acid/glycolic acid of about 50:50.

Drug agents which may be delivered by the present invention include drugs which act on the peripheral nerves, adrenergic receptors, cholinergic receptors, the skeletal muscles, the cardiovascular system, smooth muscles, synoptic sites, neuroeffector junctional sites, endocrine and hormone systems, the immunological system, the reproductive system, the skeletal system, autacoid systems, the alimentary and excretory systems, the integumentary system, the respiratory system, hematopoietic system, the histamine system and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, non-steroidal anti-inflammatory agents, anticonvulsants, ocular drugs, antihistamines, antituberculosis agents, cholinergic agents, anticholinergic agents, sympathomimetic agents, sympatholytic agents, antihypertensive drugs, vasodilators, tranquilizers, antidepressant drugs, anticoagulants, cardiac drugs, anticonvulsants, bronchodilators, expectorants, genitourinary smooth muscle relaxants, vitamins, hemostatics, antithyroid agents, heavy metal antagonists, stimulants, sedatives, antiemetics, autonomic drugs, autonomic drugs, GI drugs, electrolytes, neuromuscular blocking agents, dermatologic agents, semi-synthetic and synthetic analogs of these species.

Examples of drugs which may be delivered by the composition of the present invention include, but are not limited to antihistamines (e.g., azatadine maleate, brompheniramine maleate, carbinoxamine maleate, chlorpheniramine maleate, dexchlorpheniramine maleate, diphenhydramine hydrochloride, doxylamine succinate, methdilazine hydrochloride, promethazine, trimeprazine tartrate, tripelennamine citrate, tripelennamine hydrochloride, triprolidine hydrochloride, cetirizine, clemastine, fexofenadine); phenothiazines (e.g., prochlorperazine); nicotinic receptor antagonists (e.g., mecamylamine hydrochloride); antibiotics (e.g., penicillin V potassium, cloxacillin sodium, dicloxacillin sodium, nafcillin sodium, oxacillin sodium, carbenicillin indanyl sodium, oxytetracycline hydrochloride, tetracycline hydrochloride, clindamycin phosphate, clindamycin hydrochloride, clindamycin palmitate hydrochloride, lincomycin hydrochloride, novobiocin sodium, nitrofurantoin sodium, metronidazole hydrochloride, erythromycin, acetyl sulfisoxazole); anti-viral agents (e.g., zidovudine); antihelmintics (e.g., piperazine); antituberculosis agents (e.g., isoniazid, rifampin, ethambutol, streptomycin); cholinergic agents (e.g., chlorine chloride, acetylcholine chloride, methacholine chloride, carbachol chloride, bethanechol chloride, pilocarpine, muscarine); anticholinesterase agents (e.g., ambenonium chloride, neostigmine bromide, pyridostigmine bromide, epdrophonium); antimuscarinics (e.g., atropine, scopolamine, anisotropine methylbromide, ipratropium bromide, clidinium bromide, cyclopentolate hydrochloride, tropicamide, pirenzepine, dicyclomine hydrochloride, glycopyrrolate, hexocyclium methylsulfate, homatropine methylbromide, hyoscyamine sulphate, methantheline bromide, hyoscine hydrobromide, oxyphenonium bromide, propantheline bromide, tridihexethyl chloride, isopropamide iodide); sympathomimetics (e.g., isoproterenol, phenylethylamine, norepinephrine, dobutamine, colterol, ethylnorepinephrine, isoproterenol, isoetharine, metaproterenol, terbutaline, metaraminol, phenylephrine, tyramine, prenalterol, methoxamine, albuterol, mephentermine, propylhexedrine, bitolterol mesylate, ephedrine, ephedrine hydrochloride, ephedrine sulphate, orciprenaline sulphate, phenylpropanolamine, pseudoephedrine hydrochloride, ritodrine hydrochloride, salbutamol sulphate); sympatholytic agents (e.g., phenoxybenzamine hydrochloride); anti-motion sickness agents (e.g., diphenidol, meclizine hydrochloride, scopolamine); iron preparations (e.g., ferrous gluconate, ferrous sulphate, iron dextran); haemostatics (e.g., aminocaproic acid); cardiac drugs (e.g., acebutolol hydrochloride, diltiazem hydrochloride, disopyramide phosphate, flecainide acetate, procainamide hydrochloride, propranolol hydrochloride, quinidine gluconate, timolol maleate, tocainide hydrochloride, verapamil hydrochloride; erythrityl tetranitrate, milrinone, nimodipine, nitrendipine, nisoldipine, nicardipine, felodipine, lidoflazine, tiapamil, gallopamil, amlodipine, mioflazine); antihypertensive agents (e.g., clonidine hydrochloride, hydralazine hydrochloride, metoprolol tartrate, lisinopril, enalapril, enalaprilat, captopril, ramipril; minoxidil); vasodilators (e.g., papaverine hydrochloride, epoprostenol); non-steroidal anti-inflammatory agents (e.g., choline salicylate, magnesium salicylate, meclofenamate sodium, naproxen sodium, tolmetin sodium, ketoprofen, ibuprofen, diflunisal, flurbiprofen, fenufen, fluprofen, alclofenac, mefenamic acid, flufenamic acid); COX-2 inhibitors (e.g., celecoxib, rofecoxib); diuretics (e.g., mannitol, acetazolamide, methazolamide, bendroflumethiazide, metolazone, chlorothiazide, indapamide, ethacrynic acid, furosemide, bumetanide, spironolactone, amiloride); opiate agonists (e.g., codeine hydrochloride, codeine phosphate, codeine sulphate, dextromoramide tartrate, hydrocodone bitartrate, hydromorphone hydrochloride, pethidine hydrochloride, methadone hydrochloride, morphine sulphate, morphine acetate, morphine lactate, morphine meconate, morphine nitrate, morphine monobasic phosphate, morphine tartrate, morphine valerate, morphine hydrobromide, morphine hydrochloride, fentanyl, sufentanil, remifentanil, butorphanol, buprenorphine, alfentanil, propoxyphene hydrochloride); opiate antagonists (e.g., naloxone hydrochloride, naltrexone hydrochloride, nalorphine, levallorphan); anticonvulsants (e.g., carbamazepine, phenyloin sodium, troxidone, ethosuximide, valproate sodium, trimethadione, phenacemide, acetazolamide, progabide); dopaminergic agonists (e.g., dopamine, apomorphine, pergolide, bromocriptine, lisuride); stimulants (e.g., amphetamine, benzphetamine hydrochloride, dextroamphetamine sulphate, dextroamphetamine phosphate, diethylpropion hydrochloride, fenfluramine hydrochloride, methamphetamine hydrochloride, methylphenidate hydrochloride, phendimetrazine tartrate, phenmetrazine hydrochloride, caffeine citrate); sedatives (e.g., hydroxyzine hydrochloride, methyprylon); expectorants (e.g., potassium iodide); antiemetics (e.g., benzaquinamide hydrochloride, metoclopramide hydrochloride, trimethobenzamide hydrochloride, ondansetron, granisetron); GI drugs (e.g., ranitidine hydrochloride, cimetidine, famotidine, nizatidine, esomeprazole magnesium, rabeprazole); statins (e.g., atorvastatin, simvastatin, pravastatin, fluvastatin, lovastatin, cerivastatin); heavy metal antagonists (e.g., penicillamine, penicillamine hydrochloride); antithyroid agents (e.g., methimazole); genitourinary smooth muscle relaxants (e.g., flavoxate hydrochloride, oxybutynin hydrochloride); anticholinesterase agents (e.g., physostigmine, neostigmine, edrophonium, isoflurophate); neuromuscular blocking agents (e.g., tubocurarine, alcuronium, metocurine iodide, gallamine triethiodide, pancuronium bromide, vercuronium bromide, atracurim besylate, succinylcholine chloride, hexafluorenium bromide, alcuronium chloride, fazadinium bromide, decamethonium bromide); ganglionic stimulants (e.g., nicotine, lobeline, tetramethylammonium); ganglionic blocking agents (e.g. hexamethonium, trimethaphan); alpha adrenergic receptor antagonists (e.g., phentolamine, tolazoline, prazosin, terazosin, doxazosin, trimazosin, yohimbine, indoramin); beta adrenergic receptor antagonists (e.g., propranolol, metoprolol, nadolol, atenolol, timolol, esmolol, pindolol, acebutolol, labetalol); anesthetic agents (e.g. bupivacaine, lidocaine, tetracaine, mepivacaine, levobupicaine, prilocaine, articaine, chloroprocaine, etidocaine, cocaine, halothane, enfluranem, isoflurane, propofol, procaine methoxyflurane); benzodiazepines (e.g., alprazolam, brotizolam, chlordiazepoxide, clobazam, clorazepate, demoxepam, diazepam, flumazenil, flurazepam, halazepam, lorazepam, midazolam, nitrazepam, nordazepam, oxazepam, prazepam, quazepam, temazepam, triazolam); barbiturates (e.g., amobarbital, amylbarbitone, sodium, seocbarbital, aprobarbital, butabarbital, butalbital, mephobarbital, entobarbital, phenobarbital, secobarbital, talbutal, thiopental, thiamylal); sedative-hypnotic agents (e.g., chloral hydrate, ethchlorvynol, ethinamate, glutethimide, meprobamate, methyprylon, paraldehyde); antipsychotic agents (e.g., lithium, thiothixene, chlorpromazine, triflupromazine hydrochloride, mesoridazine besylate, thioridazine hydrochloride, acetophenazine maleate, fluphenazine, perphenazine, trifluoperazine hydrochloride, chlorprothixene, thiothixene hydrochloride, haloperidol, loxapine succinate, molindone hydrochloride, pimozide); antidepressants (e.g., imipramine, amitriptyline, trimipramine, doxepin, desipramine, nortriptyline, protriptyline, amoxapine, desipramine, maprotiline, trazodone, fluoxetine, isocarboxazid, phenelzine sulfate, tranylcypromine sulfate, venlafaxine); anticholinergic agents (e.g., benztropine mesylate, trihexyphenidyl hydrochloride, procyclidine hydrochloride, biperiden, ethopropazine hydrochloride); antitussive agents (e.g., dextromethorphan, benzonatate, pholcodine, levopropoxyphene napsylate); adrenocortical steroids (e.g., dexamethasone, hydrocortisone, beclomethasone, betamethasone, cortisone acetate, flunisolide, methylprednisolone, prednisone, prednisolone, triamcinolone); androgens (e.g., testosterone, nandrolone, danazol, fluoxymesterone, stanozolol, testolactone); antiandrogens (e.g., cyproterone acetate, flutamide, finasteride); beta-adrenergics (e.g., formeterol, isoproterenol, albuterol, bitolterol, salmeterol); Gonadotropin-releasing hormone analogs (e.g., leuprolide, goserelin, buserelin); Mediator-release inhibitors (e.g., cromolyn sodium, nedocromil sodium); anti-leukotriene drugs (e.g., zafirlukast, zileuton, montelukast); progestins (e.g., progesterone, hydroxyprogesterone, medroxyprogesterone, ethynodiol diacetate, norethindrone, norethynodrel, norgestrel, megestrol acetate); pregnadienes (e.g., chlormadinone acetate); antiprogestins (e.g., mifepristone); estrogens (e.g., estradiol, ethinyl estradiol, mestranol, quinestrol, diethylstilbestrol, chlorotrianisene); antiestrogens (e.g., clomiphene, tamoxifen); sulfonylureas (e.g., tolbutamide, chlorpropamide, glyburide, glipizide, gliclazide, tolazamide); diabetic agents (e.g., phenformin, ciglitazone); antiplatelet drugs (e.g., dipyridamole, ticlopidine); thrombolytic agents (e.g., streptokinase, urokinase, alteplase); anticoagulants (e.g. warfarin, anisindone, dicumarol, diphenadione erythrityl tetranitrate, heparin, tinzaparin, enoxaparin); hormones (e.g., Thyroid stimulating hormone, Luteinizing hormone, Follicle-stimulating hormone, Chorionic gonadotropin, Thyrotropin-releasing hormone, calcitonin, insulin); corticotrophins (e.g., Adrenocorticotropic hormone); Growth hormone-releasing hormone (e.g., somatostatin); methylxanthines (e.g., theophylline, caffeine, aminophylline); antispastic agents (e.g., tizanidine); vitamins (e.g., folate, thiamine hydrochloride, ascorbic acid, clacitriol; menaquinone, phytonadione); anti-gout agents (e.g., colchicine, allopurinol); bisphosphonates (e.g., risedronate, etidronate, tiludronate); antineoplastics (e.g., temozolomide, targretin, vincamine, methotrexate, vincristine, cyclophosphamide, etoposide, mechlorethamine, cyclosporine, vinblastine, fluorouracil); chemoprotectants (e.g., amifostine); antipsoriatic agents (e.g., acitretin); anti-dementia agents (e.g., rivastigmine, donepezil, tetrahydroaminoacridine); uterine stimulants (e.g., ergonovine, methylergonovine); antimigraine agents (e.g., dihydroergotamine, ergotamine); glycoproteins (e.g., erythropoietin); Colony Stimulating Factors (e.g., filgrastim); enzymes (e.g., algluc-erase, L-aspraginase); polypeptides (e.g., glucagon); cytokines (e.g., alpha interferon, beta interferon); vaccines (e.g., Bacillus Calmette-Guerin); ocular drugs (e.g., timolol maleate, dorzolamide, betaxolol, dipivefrin, pilocarpine, latanoprost, unoprostone, brinzolamide, travoprost); dermatologic agents (e.g. isotretinoin, etretinate, tretinoin, betamethasone dipropionate, clobetasol propionate, fluocinolone acetonide); antiparkinson drugs (e.g., levodopa, carbidopa, tolcapone); antiurolithic agents (e.g., tiopronin); unclassified agents (e.g., amantadine hydrochloride, leucovorin calcium, methylene blue, pralidoxime chloride, diazoxide, etintidine, tetatolol, sildenafil, phenaglycodol); serotonin agonists and antagonists, other substances including all of the major therapeutics such as agents for the common cold, anti-addiction, anti-allergy, anti-emetics, anti-obesity, antiosteoporeteic, anti-infectives, anti-virals, analgesics, anesthetics, anorexics, anti-arthritics, antiasthmatic agents, oligosaccharides, enkephalins and other opioid peptides, low molecular weight heparins, dermatologic agents, anticonvulsants, antidepressants, electrolytes, thrombolytics, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

The therapeutic agent to be intracutaneously delivered in accordance with the method of the present invention may be vaccines and the like used in the prevention, diagnosis, alleviation, treatment, or cure of disease. Examples of proteins and proteinaceous compounds which may be formulated and employed in the delivery system according to the present invention include those proteins which have biological activity or which may be used to treat a disease or other pathological condition. They include, but are not limited to hormones, growth hormone, Low molecular weight heparin, Factor VIII, Factor IX and other coagulation factors, chymotrypsin, trypsinogen, alpha-interferon, beta-galactosidase, lactate dehydrogenase, growth factors, clotting factors, enzymes, immune response stimulators, cytokines, lymphokines, interferons, immunoglobulins, retroviruses, interleukins, peptides, somatostatin, somatotropin analogues, somatomedin-C, Gonadotropic releasing hormone, follicle stimulating hormone, luteinizing hormone, LHRH, LHRH analogues such as leuprolide, nafarelin and goserelin, growth hormone releasing factor, gonadotropins such as chorionic gonadotropin, oxytocin, octreotide, somatotropin plus an amino acid, vasopressin, adrenocorticotrophic hormone, epidermal growth factor, prolactin, somatotropin plus a protein, cosyntropin, lypressin, polypeptides such as thyrotropin releasing hormone, thyroid stimulation hormone, calcitonin and analogs, secretin, pancreozymin, enkephalin, glucagon, endocrine agents secreted internally and distributed by way of the bloodstream, and the like. Other agents which may be encased and delivered include .alpha.sub.1 antitrypsin, insulin and other peptide hormones, adrenal cortical stimulating hormone, thyroid stimulating hormone, and other pituitary hormones, interferon .alpha., .beta. and .delta., erythropoietin, growth factors such as GCSF, GM-CSF, M-CSF, insulin-like growth factor 1, tissue plasminogen activator, CF4, dDAVP, tumor necrosis factor receptor, pancreatic enzymes, lactase, interleukin-1 receptor antagonist, interleukin-2, tumor suppresser proteins, cytotoxic proteins, viruses, viral proteins, recombinant antibodies and antibody fragments, Epidermal growth factors, Erythropoietin and analogs, Follicle stimulating hormone, G-CSF, Glucagon, GM-CSF, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leuteinizing hormone, Leutenizing hormone releasing hormone and analogs, Alpha-1 anti-trypsin, Anti-Angiogenesis agents, Antisense, Monoclonal antibodies, Parathyroid hormone and analogs, Parathyroid hormone antagonists, Prostaglandin antagonists, Prostaglandins, Recombinant soluble receptors, tissue plasminogen activators, TNF-, and TNF-antagonist, and the like. Analogs, derivatives, antagonists, agonists, and pharmaceutically acceptable salts of the above may also be used.

The protein compounds useful in the formulations of the present invention can be used in the form of a salt, preferably a pharmaceutically acceptable salt. Useful salts are known to those skilled in the art and include salts with inorganic acids, organic acids, inorganic bases, or organic bases.

Table 1 provides examples of drugs, with the expected dose necessary to achieve a therapeutic effect, and the total volume of injection (of the ultra-concentrated therapeutic formulations of the present invention) which is injected into the patient in accordance with the teachings of the present invention.

TABLE 1

| Drug | Dose | Volume of Injection |
| --- | --- | --- |
| Vaccines | 5-50 µg | <100 nl |
| IFN-α | 12 µg | 0.024 µl |
| FSH | 15 µg | 0.030 µl |
| EPO | 40 µg | 0.080 µl |
| IFN-β | 44 µg | 0.088 µl |
| IFN/PEG | 70 µg | 0.140 µl |
| PTH | 20 µg | 0.200 µl |
| GLP | 0.5 mg | 1 µl |
| Glucagon | 1.0 mg | 2 µl |
| hGH | 1.5 mg | 3 µl |
| Insulin | 1.5 mg | 3 µl |
| hGH/S.R. | 7.5 mg | 70 µl |

Table 2 provides an illustration of the relative unit doses of various therapeutic agents contemplated for use in connection with the injection device and methods of the present invention.

TABLE 2

RELATIVE UNIT DOSES OF VARIOUS THERAPEUTIC AGENTS

| 100 µg | 1 mg | 10 mg-100 mg |
| --- | --- | --- |
| FSH | Insulin | Monoclonal antibodies |
| IFNs | Growth hormone | Sustained |
| Interleukins | Glucagon | Release |
| CSFs | GLP 1 | |
| Calcitonin | | |
| Vaccines | | |

In preferred embodiments of the present invention, the therapeutic agent is dried into a non-structured, densified state and surrounded with a pharmaceutically acceptable carrier to form a fluidized solid of minimal injection volume. In certain preferred embodiments, the dried therapeutic agent is processed in order to decrease its particle size by any pharmaceutically acceptable manner known to those skilled in the art. Various methods of particle size manipulation and/or reduction may be utilized in order to prepare the therapeutic formulations useful in the present invention. Such particle size reduction procedures include comminution processes (cutting, chopping, crushing, grinding, milling, micronizing, nanosizing, freeze drying, spray-freeze-drying, trituration, and microfluidization).

The concentrated solid particulates included in the injectable formulations of the invention preferably range in diameter from the nanometer size to particles just large enough to fill into the needle (e.g., the particles should be smaller than the inner diameter of the needle). In the extreme, the upper end on particle size is the diameter of the largest injection needle applied, though typically particles are less that $1/10^{th}$ the diameter of the inner diameter of the needle used.

In preferred embodiments, the therapeutic agent is processed in order to decrease its particle size to a mean particle size range from 10 nanometers (0.01 microns) to about 250 microns, with no particles being larger than about 1 mm. In more preferred embodiments, the particle size of the therapeutically active agent is reduced to a mean particle size from about 0.1 microns to about 25 microns, with no particles being larger than about 50 microns, and in certain embodiments the particles are most preferably from about 1 to about 10 microns. By reducing the particle size of the solid particles to this range, the diameter of the largest particles are small enough to pass through the diameter of the largest injection needle useful in connection with the present invention.

Spray drying techniques are well known to those skilled in the art. Spray drying includes the steps of atomization of a solution containing one or more solid (e.g., therapeutic agent) via a nozzle spinning disk, or other device, followed by evaporation of the solvent from the droplets. The nature of the powder that results the function of several variables including the initial solute concentration, size distribution of droplets produced and the rate of solute removal. The particles produced may comprise aggregates of primary particles which consist of crystals and/or amorphous solids depending on the rate and conditions of solvent removal.

A spray-drying process for preparing ultra-fine powders of biological macromolecules such as proteins, oligopeptides, high molecular weight polysaccharides, and nucleic acids is described in U.S. Pat. No. 6,051,256. Freeze-drying procedures are well known in the art, and described, for example, in U.S. Pat. No. 4,608,764 and U.S. Pat. No. 4,848,094. Spray-freeze-drying processes are described, e.g., in U.S. Pat. No. 5,208,998. Other spray-drying techniques are described, for example, in U.S. Pat. Nos. 6,253,463; 6,001,336; 5,260,306; and International Patent Publication Nos. WO91/16882 and WO 96/09814.

Lyophilization techniques are well known to those skilled in the art. Basically, lyophilization is a dehydration technique which takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, therefore, thermally labile products can be preserved. Steps in freeze drying include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products", and are described, e.g., in U.S. Pat. No. 6,199,297. "Standard lyophilization conditions, are described, e.g., in U.S. Pat. No. 5,031,336, and in "Freeze Drying of Pharmaceuticals" (DeLuca, Patrick P., J. Vac. Sci. Technol., Vol. 14, No. 1, January/February 1977); and "The Lyophilization of Pharmaceuticals: A Literature Review" (Williams, N. A., and G. P. Polli, Journal of Parenteral Science and Technology, Vol. 38, No. 2, March/April 1984).

In certain preferred embodiments, the lyophilization cycle is partially performed above the glass transition temperature (Tg) of the therapeutic agent formulation to induce a collapse of the mass to form a dense cake containing residue moisture. In contrast, in typical prior art methods, the primary drug lyophilization is carried out below the glass transition temperature in order to avoid a collapse in order to achieve a complete drying of the particles. The residual moisture contained in dense cake formed by this preferred method is removed by placing the collapsed cake into solution of semi- (or minimal aqueously miscible, pharmaceutically acceptable carrier. The carrier then can be removed or used as the fluidity carrier for injection of the therapeutic formulation.

In certain preferred embodiments where the therapeutic agent comprises a bioactive agent (e.g., one or more proteins, peptides, polypeptides, etc.), a carrier compound comprising a stabilizing polyol is included in the formulation which is to be dried. Such formulations and materials are described for example in U.S. Pat. Nos. 6,290,991 and 6,331,310, both of which are hereby incorporated by reference.

Once the therapeutic agents are ultra-concentrated, for example, in the manners set forth above, they are then fluidized for injection, preferably in a carrier with special rheologic properties in order to facilitate administration. The ultra-concentrated solid is preferably surrounded by a non-aqueous or a semi-aqueous carrier in order to promote stability and aid in complete injection of the dose. In preferred embodiments, the term "fluidized for injection" means that the solid content of the dose for injection is from about 1 to about 99 percent, by weight, and more preferably from about 50 to about 85% by weight.

In contrast to standard subcutaneous injections, where the injection volumes range from 0.3-1.2 ml (equivalent to 300-1200 microliters), the injection volumes contemplated for use in conjunction with the present invention range from about 0.1 to about 10 microliters. This is accomplished via the use of the ultra-concentration technology in order to allow for a low-volume, shallow injection through a fine needle. In preferred embodiments the needle is 27 to 30 gauge, and has a inner diameter of about 0.33 mm. The injection is preferably made to a depth in the skin from about 300 microns to about 500 microns.

The pharmaceutically acceptable carrier (i) acts to protect the concentrated therapeutic agent by shielding it from excess moisture; (ii) enables injectability by providing a medium in which dry particles can flow by lubricating the drug mass and injection chamber to allow delivery at reasonable injection forces and to prevent clogging of the needle, and (iii) preferably provides the capability of variable dosing by preventing separation of the formulation components during administration. Preferably, the resultant formulation has thixotropic properties.

In preferred embodiments, the pharmaceutically acceptable carrier is a non-solvent for the dried particulate formulation, and is preferably non-aqueous or semi-aqueous. Such carriers significantly prolong this shelf-life of the therapeutic agent in concentrated form (e.g., lyophilized proteins) stored at ambient conditions. This is accomplished in part because such carriers repel oxygen and water. Examples of suitable pharmaceutically acceptable carriers include alkyl benzoates, aryl benzoates, aralkyl benzoates, triacetin, dimethyl sulfoxide (DMSO), or N-methyl-2-pyrrolidone (NMP). In embodiments where the therapeutic agent is hydrophobic, the pharmaceutically acceptable carrier may be aqueous in nature.

In one preferred embodiment where the therapeutic agent comprises one or more proteins, the protein(s) and a minimal amount of pharmaceutically acceptable excipients are lyophilized to form an amorphous (non-structured) solid mass having a low volume (per unit dose). These formulations minimize the amount of carbohydrate, buffer capacity and non-specific binding agents needed to stabilize the protein. In contrast, typical lyophilization solutions comprise, in addition to the protein, carbohydrate, buffers, solution stabilizers, bulking agents, dissolution agents, and non-specific binding agents. Bulking agents required for particle formulation, process metering and flowability are not needed in the formulations of the present invention. Similarly, solution stabilizers are not required. By eliminating bulking agents and solution stabilizers as well as reducing the amounts of other ingredients needed to prepare a suitable injection media for proteins, the proposed injection volume can be greatly reduced as compared to current volumes for injection of proteins. In certain embodiments where the therapeutic agent is a protein, the pure protein may be used alone, if stable, or with a minimal amount of stabilizer and buffering agent, e.g., approx. 0-3% by weight. The more concentrated the protein when dry (e.g., from about 25 to about 60% protein solids), the less carbohydrate is needed.

In certain preferred embodiments, a polymeric element is incorporated into the non-aqueous or semi-aqueous carrier in order to add structure to the liquid. By adding such polymers, e.g., polylactic acids, polyglycolic acids, polylactic-co-glycolic acids, polyanhydrides, polyorthoesters, and combinations thereof, two unique rheologic properties are provided to the injectable formulations of the present invention. First, with respect to shear which occurs as the formulation is injected from the injection device, as the mass begins to flow out of the needle the carrier viscosity reduces the injection force required to force all of the injection dose out of the needle. Second, the injection of a polymer in addition to promoting drug flow prevents settling of the solid drug within the carrier. These properties (shear thinning liquid and rest shear) combine to accomplish dose proportionality.

Injection Device

During epidermal and dermal administration, there is a need to limit the depth of needle penetration to avoid subcutaneous injection and to reliably fix the orientation of the needle to the skin. The pain felt during epidermal and dermal injection is caused by a combination of trauma to the pain receptors, distension of the tissues by the drug, and muscle tension caused by pain anticipation. The standard epidermal or dermal injection results in injection of the needle into the skin at an angle of about 10-15 degrees. By inserting the needle at this angle, about 5 mm to about 6 mm of the needle is inserted into the skin, significantly disrupting pain receptors located throughout the epidermal and dermal layers. In certain preferred embodiments, the present invention utilizes a thin walled, custom designed needle to place drug into the epidermal or dermal layer.

Standard injections are given into the subcutaneous or intramuscular region of a patient. These deep locations are targeted because the tissue expands more easily, relative to shallow dermal sites, to accommodate the 0.1-1.0 ml injection volumes required by most therapeutic injectables. Injection of large viscous volumes tends to cause more pain than small dilute volumes. However, viscous medications have not been administered epidermally or dermally in the past because a large lumen needle is required. Such needles cannot be used for epidermal or dermal administration. Additionally, liquid formulations must be injected slowly epidermally or dermally to avoid tissue damage and volumes greater than 0.5 ml cannot be administered into the epidermis or dermis.

The stratum corneum (or upper most layer of the skin) is relatively thin—only 5-15 microns. This invention employs a thin walled, custom designed needle to place drug into the epidermal or dermal layers as space is not abundant and the skin does not expand as freely as the subcutaneous space (a typically fatty region). Therefore a minimal injection volume is used.

To date, the procedure typically used for epidermal or dermal injection is difficult to perform. The skin must be stretched at the injection site. The syringe and needle with its bevel up are positioned almost flat against the skin. The needle is advanced inserted approximately ⅛ inch into the skin at an angle of from around 10-15 degrees relative to the plane of the skin to form a blister or wheal containing the substance. The technique generally requires the skills of a trained nurse or physician, thereby precluding self-administration. A needle that penetrates the skin greater than about 3.0 mm has a potential of passing through the dermis layer into the subcutaneous layer. Therefore, the needle length must be no greater than ⅜ inch. Conversely, the needle can penetrate at too shallow a depth resulting in reflux of the substance from the injection site, commonly known as a "wet injection". For epidermal or dermal injection, the skin should be stretched at the site.

In preferred embodiments, the injection device used in the present invention is adapted for epidermal or dermal injection of the ultra-concentrated unit doses described above. In preferred embodiments, the device is pre-filled with the injectable dose of therapeutic agent in, e.g., a slurry or paste. The injection device is specifically adapted to precisely meter the low volume of unit dose to be injected.

In preferred embodiments, the injection needle is from about 27 to about 30 gauge. In such embodiments, the thickness of the needle is minimized in order to avoid a sensation of pain upon administration of the therapeutic agent. However, it is further contemplated in other embodiments where avoidance of low levels of pain is not essential so that larger gauge needles can be utilized in conjunction with the formulations and methods of the present invention.

Highly concentrated slurry or paste formulations typically display poor flow properties in standard syringes and therefore, novel needle/syringe designs are required.

In preferred embodiments, the unit dose injectable formulation comprising a slurry or paste of the therapeutic agent is loaded directly into the needle of the injection device, and substantially the entire unit dose is displaced from the drug needle during injection of the unit dose into the epidermis or dermis of the patient. In order to accomplish this, the injection device preferably incorporates a plunger that acts in a way that the full amount of the loaded therapeutic formulation is loaded into the lumen of the needle and is pushed out into the patient upon administration using a positive displacement design.

The plunger may comprise, for example, an application rod which fits within the lumen of the needle which is displaced from its resting position toward the end of the needle upon activation (e.g., a displacement force enacted by the patient or by the person administering the injection) in such a manner that substantially all (e.g., approaching or equal to 100%) of the loaded therapeutic formulation is pushed out of the needle and into the location of injection (e.g., epidermis or dermis). The application rod itself may be made of any suitable material known to those skilled in the art, including metal or plastic. The plunger may be, e.g., a piece of wire that fits in the inner diameter of the needle. The length of the plunger (e.g., wire) may be equivalent to the length of the needle lumen that is desired to be swept free of the loaded therapeutic formulation. Thus, for example, upon actuation of the injection device, the plunger moves downward through the needle lumen for a distance equivalent to the length of semisolid therapeutic formulation which is to be pushed out of the needle tip and into the epidermal or dermal layer of the patient. In certain preferred embodiments, the tip of the plunger is a deformable gel (e.g., a thermoplastic elastomer such as Santoprene®) so that the tip of the plunger can sweep tightly against the inner wall of the needle lumen and can deform to meet the surface of the inner wall in embodiments where the diameter of the needle lumen changes along its length, thereby ensuring clearance of the semisolid therapeutic formulation as the plunger moves downward to expel the formulation from the needle during use.

In alternative embodiments of the invention, the plunger is a deformable gel. The deformable gel is deformed upon actuation of the injection device and is forced downward toward the tip of the needle thereby displacing the slurry or paste of therapeutic formulation unit dose. Suitable materials to form deformable gels useful in the present invention are known to those skilled in the art. Examples include gels formed form the polymeric materials mentioned previously herein with respect to carriers for the therapeutic agent. Specific examples include thermoplastic elastomers (such as a suitable grade of Santoprene®), a polyacryl amide or agarose gels having sufficient rigidity to act as a plunger; and elastomeric silicon gels having the requisite rigidity, which are very biocompatible and have been used e.g. in long-term human implants.

In certain preferred embodiments, the needle portion of the injection device is from about 6 to about 8 cm in length, thereby providing a lumen having a sufficient interior volume to contain the dose of semisolid therapeutic formulation and the plunger.

In further preferred embodiments, a custom needle design is employed with the device in order to eliminate potential coring affects upon application of the needle into the skin. In such embodiments, the extreme tip of the needle is disposed in a closed-ended orientation such that a peak is created by which to puncture the skin. Upon actuation of the injection device, the force of the loaded therapeutic formulation to be dispensed enlarges the tip of the needle (once the stratum corneum is penetrated), leaving a route through which the formulation is displaced out of the tip of the needle. The tip of the needle can be manufactured in any fashion known to those skilled in the art to achieve a flat orientation (e.g., having a beveled, close-ended or sealed end) which is capable of being outwardly displaced during actuation to enable the therapeutic formulation to be ejected from the device. For example, in certain preferred embodiments, the extreme tip of the needle is crimped into closed-ended orientation to create a peak by which to puncture the skin. The force of the therapeutic formulation being dispensed through the needle opens the needle crimp once the stratum corneum is penetrated, thereby allowing the therapeutic formulation to be displaced out of the tip of the needle.

In certain preferred embodiments, the injection device may incorporate multiple needle systems in which multiple penetrations are made to the skin, simultaneously administering a larger dose of drug while maintaining small individual volumetric injections. Such devices can be utilized in situations where the amount of therapeutic agent to be administered cannot be readily incorporated into a single needle utilized in the invention or where a greater exposure of antigen presenting cells in warranted as in vaccination.

In yet further embodiments of the invention, the upper portion of the needle is widened in a smooth manner (relative to the tip portion of the needle), in order to hold more volume of the therapeutic formulation. In this manner, additional amounts of the therapeutic agent can be administered via the use of a single needle while maintaining the small gauge of the skin-penetrating portion of the needle, thereby maintaining the benefit of decreased pain by the small needle diameter. In such embodiments, it is preferred that the plunger include a tip which is made from a deformable gel or rubber (e.g., Santoprene®) so that the tip of the plunger can deform and move past the inner shoulder of the needle lumen as it tapers toward its (pointed) end.

In yet further embodiments of the invention, the needle is spiral-shaped in order to create more space to contain the semisolid therapeutic formulation.

In further preferred embodiments, the injection device of the present invention includes a stabilizing device (e.g., a disk or ball) which holds the skin taught and the injection device is placed against the skin and activated. In further preferred embodiments, the injection device includes a biasing device (e.g., a spring) which is released upon activation of the injection device to force the needle into the skin, and a retraction spring which is activated after the injection is made in order to pull back the empty needle. In use, the user preferably sets the device against the skin, thereby automatically depressing a safety device (such as a key), which then enables the activator, (e.g., an activation button). With the stabilizing disk placed flat on the skin, the user pushes the activation button to activate the mechanism. The stabilizing disk may be made of any suitable material, e.g., Santoprene®. The needle is forced into the skin by a spring and the plunger is forced through the needle, thereby forcing the therapeutic formulation through the needle. As the therapeutic formulation is forced through the needle, the closed-ended orientation of the needle tip is expanded, thereby allowing the therapeutic formulation to flow out of the needle tip. After administration of the dose via the plunger being displaced through the needle forcing the therapeutic formulation out of the needle tip, a retraction device (e.g., a spring) is activated, thereby pulling an empty needle back into the device.

In certain preferred embodiments, the biasing device comprises a spring or other pressure source (e.g., a gas source, a piston, etc.). The retraction device may utilize a spring or the same types of pressure sources as the biasing device.

In certain preferred embodiments, the injection device further includes a dose controller which can be adjusted to change the distance that the plunger travels through the needle, thereby controlling the amount of therapeutic formulation forced through the needle tip and thereby changing the dose administered to the patient.

In further preferred embodiments, the needle is elongated with respect to a standard needle of the same gauge in order to include an additional dose within the lumen of the needle itself.

In further preferred embodiments, the needle is enclosed within an outer casing in order to hide the needle so that the patient never sees the needle prior to, during or after the injection.

In yet further embodiments, the injection device is capable of being used multiple times. In such embodiments, for example, within the housing there are multiple needles filled with a unit dose of the therapeutic agent. After actuation of the device and delivery of a unit dose, the spent needle retracts into the housing. Thereafter, the next (unused) needle is caused to move into a location where it will extend through the housing and deliver its unit dose of therapeutic formulation upon the next actuation of the delivery device.

Turning now to the Figures, FIG. 1 is a cross sectional view of an injection device in accordance with the present invention. The injection device is depicted showing the syringe 10 having arranged therein a drive spring 12, a drug tube (needle) 15, a retraction spring 13 and a plunger 14. The ultra concentrated fluidized solid comprising the therapeutic agent is loaded into the lumen of the drug tube. Upon actuating a needle insertion mechanism (not shown), the drive spring 12 is displaced in a downward direction, thereby forcing the plunger 14 against the dose 18. As the dose is moved downward through the crimp tip of 16 of the drug needle 15, the needle crimp is forced open and the dose expelled from the needle. Once this is accomplished, the retraction spring 13, which has been biased in a downward direction during the actuation, is then released in an upward direction, thereby retracting the needle.

Figure 2:
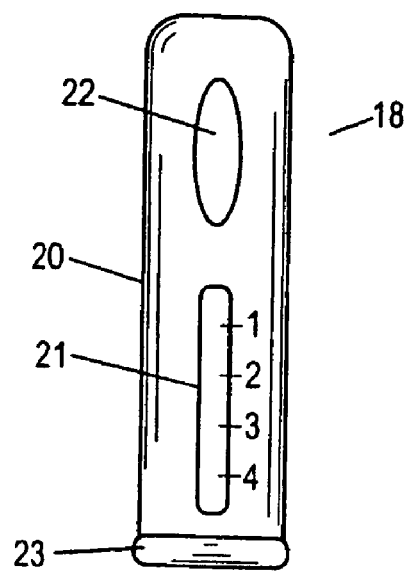
FIG. 2. is an outer side view of the injection device of FIG. 1.

FIG. 2 is an outer side view of the of the injection device of FIG. 1. In FIG. 2, the casing 20 includes a dose scale 21, a release (activation) button 22, and a release pad 23. The needle itself is hidden inside the casing of the injection device 18. In this manner the patient never sees the needle, reducing the psychosomatic pain effect of seeing an impending injection. In use, the release pad for stabilizing disc 23 is set flat against the skin of the patient. Thereafter, the user depresses the release button 22 which activates the spring mechanism, thereby forcing the needle 15 into the skin and forcing the plunger 14 through the lumen of the needle, and injecting the unit dose of therapeutic agent into the epidermal or dermal layer of skin of the patient. Upon completion, the retraction spring 13 is activated, pulling back the empty needle. With respect to FIG. 2, a dose scale 21 is depicted whereby the user can adjust the dose depending e.g., the instructions of the physician. For example, the dose scale might have control which can be set at the numbers 1, 2, 3, or 4, respectively, which in turn will change the distance that the drive spring 12 can push the plunger 14 in a downward direction. This in turn changes the amount of therapeutic formulation displaced from the needle as the distance that the plunger 14 travels corresponds to the amount of therapeutic formulation displaced.

Figure 3A:
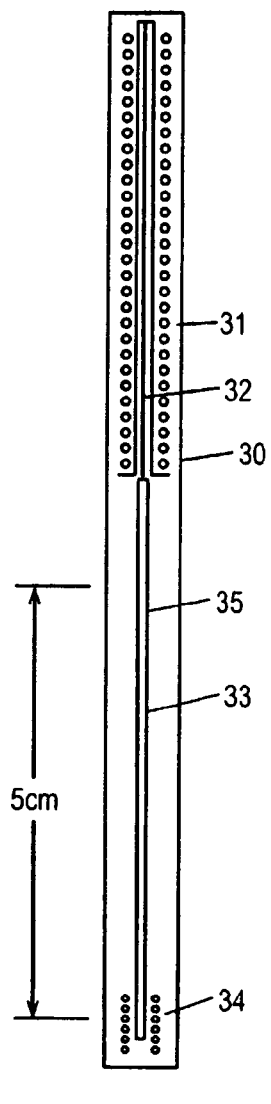
FIGS. 3a-3c are a cross-sectional view of the spring mechanism lay out of an injection device in accordance with the present invention.
Figure 3B:
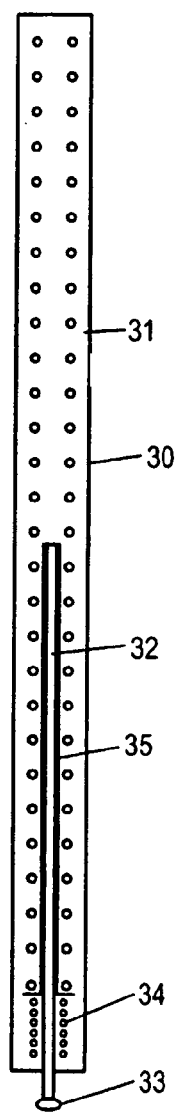
Figure 3C:
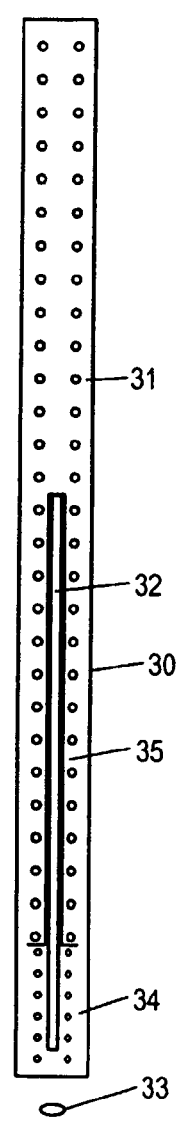

FIG. 3 is a cross sectional view of the spring mechanism lay out of an injection device in accordance with the present invention. Depicted therein is the injection device in its resting position 3A, in its activated state 3B, and after actuation 3C. The device includes a casing for housing 30, a drive spring 31, a plunger 32, a dose of therapeutic agent 33, and retraction spring 34. In its resting position (FIG. 3A) the dose of therapeutic agent 33 is located within the lumen of the needle 35. The needle is longer relative to standard epidermal or dermal needle and is 27 gauge or thinner. The dose of therapeutic agent is contained within the 5 cm length of the needle. Above the dose of therapeutic agent is the plunger 32. Upon actuation (FIG. 3B), the top drive spring 31 has extended in a downward direction, thereby advancing the needle into and through the skin (not shown in this figure), and causing the plunger 32 to push the dose of therapeutic agent through the crimp end of the needle thereby expanding the crimp end and dispensing the therapeutic agent in the epidermal or dermal flare. In the post-injection phase (FIG. 3C) the retraction spring 34 returns the needle 35 to its pre-injection position while the dose of therapeutic agent 33 remains in the body.

Figure 4A:
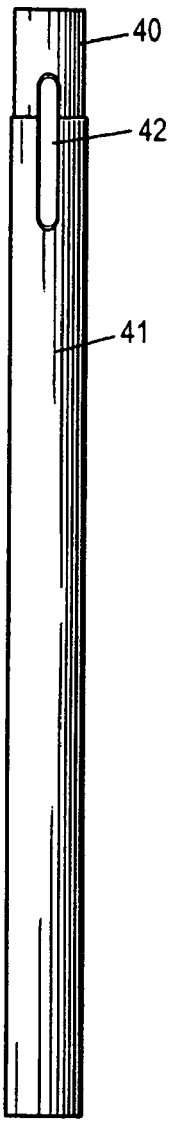
FIGS. 4a-4c are depictions of the outer housing and safety sleeve of an injection device in accordance with the present invention.
Figure 4B:
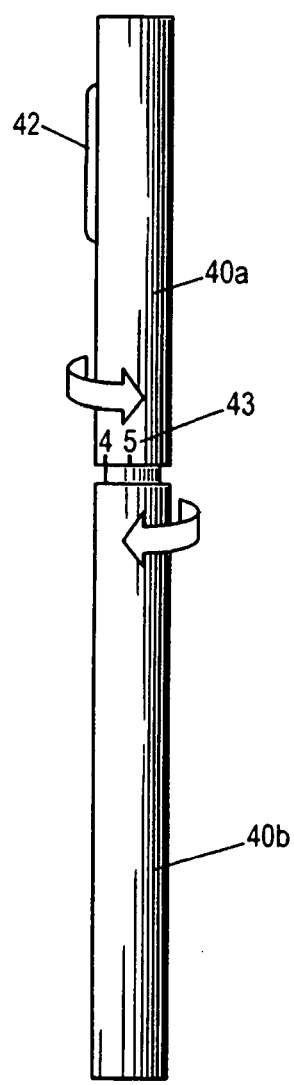
Figure 4C:
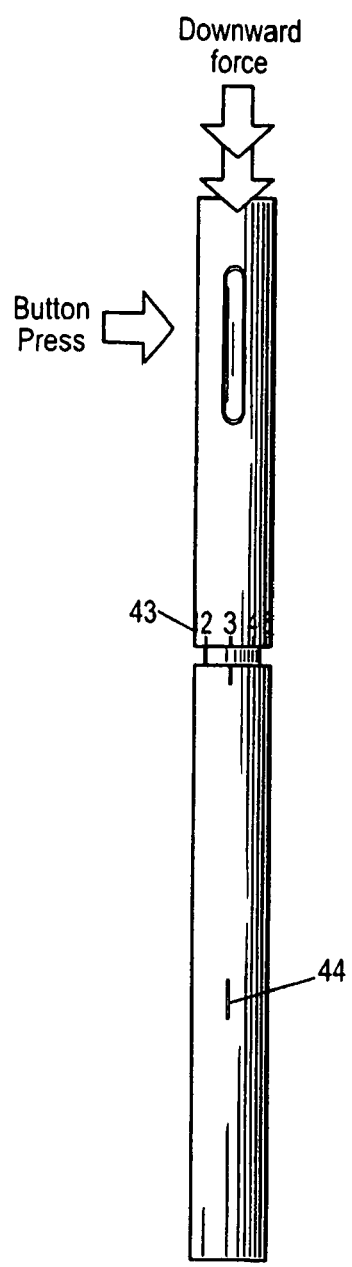

FIGS. 4A-4C are depictions of the outer housing and safety sleeve of an injection device in accordance with the present invention. Beginning with FIG. 4A, a safety sleeve 41 covers the injection device 40. The safety sleeve is removed prior to use. Preferably, the safety sleeve 41 minimizes the occurrence of accidental activation, and its removal allows the device to become "active". Next, as depicted in FIG. 4B, a dose setting 43 is selected which determines the distance the drive spring project from the injection device upon actuation, and in turn the amount of formulation delivered. In the embodiment depicted in FIG. 4C, the dose setting 43 is adjusted by turning the upper portion 40a of the device one in opposite direction to the bottom of the device 40b until, as depicted in the middle drawing, the number corresponding to the desired depth is properly aligned (in this case, depth 3). The bottom of the device (not shown) is set against the skin of the patient in desired location, and activation button 42 is depressed, thereby activating the drive spring (not shown) downward. After activation, the retraction device (not shown) retracts the needle into the injection device 40. In an optional embodiment, an indicator 44 changes colors to indicate that the device was used. For example, indicator 44 may change colors from green (prior activation) to red (after activation), indicating that the dose was delivered. In the device depicted in FIG. 4, only one dose of therapeutic agent is included in the device. After actuation, the spent injector is locked and can not be reused. For example, in one embodiment of the device of FIG. 4, the activation button applies a force to the plunger sufficient to move it to displace the drug within the needle lumen and sufficient to overcome back pressure (e.g., 76 psi) of the dermis layer during intracutaneous injection. Upon pressing the activation button, a force equal to approximately 3 lbs of pressure is achieved. This force results in release of the spring which depresses the plunger into the needle lumen thereby injecting the formulation intracutaneously. The injector is kept in place for a total of 2-5 seconds or less. The color indicator changes from green to red to indicate the dose was delivered. The spent injector is then locked and cannot be reused. In certain preferred embodiments, the injector is an auto-injector, and the syringe is a safety syringe.

Figures 5A, 5B, 5C:
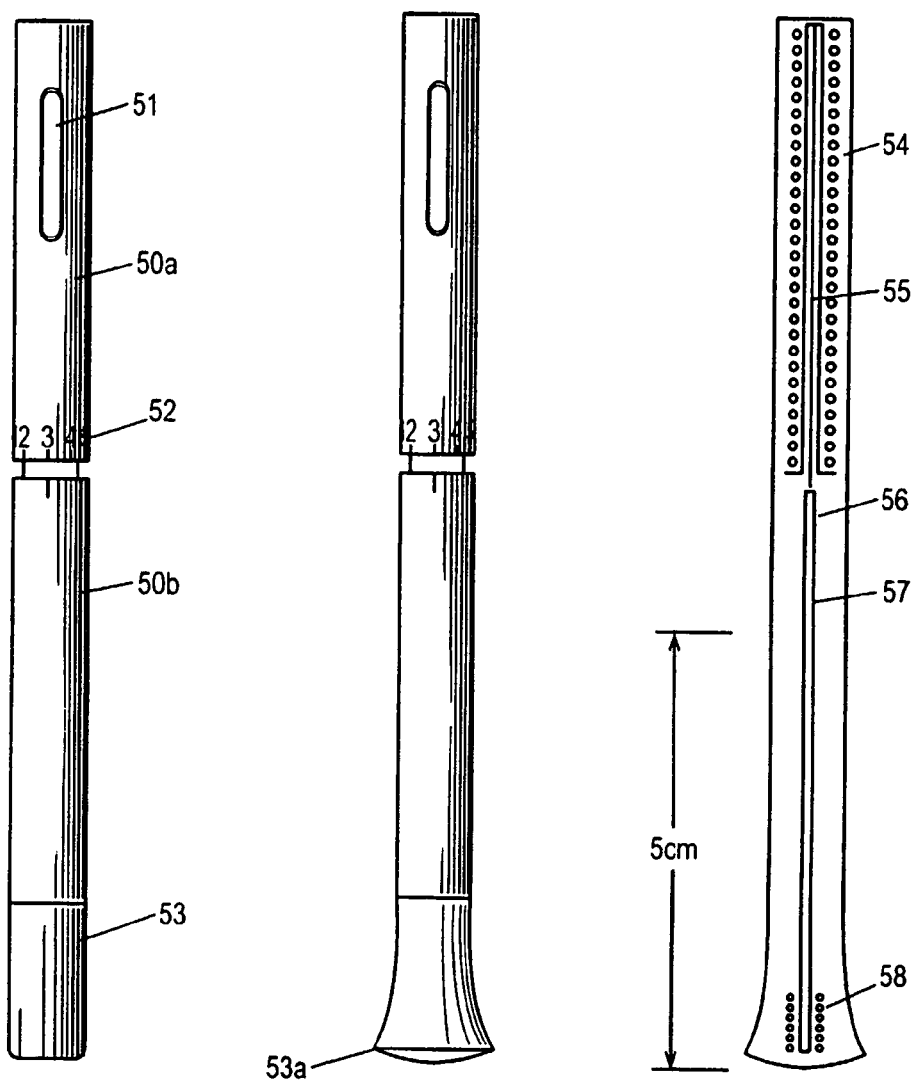
FIGS. 5a-5b are a side view of an injection device in accordance with the present invention depicting the skin/device interaction.
FIG. 5c is a cross-sectional view of the device as depicted in FIG. 5b.

FIG. 5A is a side view of an injection device in accordance with the present invention depicting the skin/device interaction. As shown in FIG. 5A, the device is in its "resting" position, wherein the device has a top casing 50a bottom portion 50b which may be turned in opposing directions to adjust the injected dose as shown by the depth setting 52. The device has an activation button 51 and a stabilizing disk 53. In the embodiments depicted in FIG. 5 the stabilizing disk is made of soft rubber (e.g., Santoprene®) and forms an extension of the casing of the injection device. As depicted in FIG. 5B, when the injection device is set against the skin of the patient, the tip 53a of the stabilizing device is deformed in an outward direction created by holding the skin at the injection site taught. FIG. 5C is a cross-sectional view of the device as depicted in FIG. 5b. As shown in FIG. 5C prior to activation, the drive spring 54 is in its retracted position; the plunger 55 is located within the needle 56 and is positioned to displace the dose of therapeutic agent of 57 when the device is activated. A retraction spring 58 is located in the opposite tip of the device. The drug is contained in a 5 cm section of the needle. In certain preferred embodiments, a safety interlock is incorporated with the stabilizing disk.

Figures 6A, 6B:
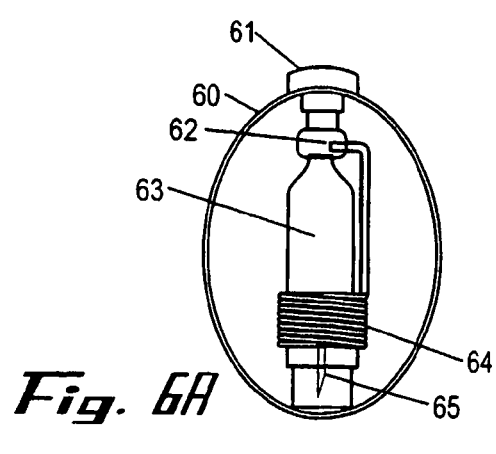
FIGS. 6a-6b depict a different embodiment of an injection device using a gas-powered auto injector in accordance with the present invention.

FIGS. 6A-6B depicts a different embodiment of an injection device in accordance with the present invention. In this embodiment the delivery of the therapeutic formulation is accomplished using a pressure source (in this case compressed gas) instead of the spring activation mechanism depicted in FIGS. 1-4. FIG. 6A is a cross sectional view of an injection device of the invention. It shows a housing 60, an activation button 61, valve 62, compressed gas cylinder 63, toroidal needle syringe 64, and needle tip 65. Depression of activation button 61 causes compressed gas to be released from gas cylinder 63 through valve 62 and into toroidal needle syringe 64, and causes the tip 65 toroidal needle 64 to be released to extend downward through the housing 60 and into the skin of a patient to the desired depth, and thereby displacing the semisolid therapeutic formulation (not shown) through the tip 65 of the needle 64 and into an intradermal skin layer of the patient. FIG. 6B is a side view of the device of FIG. 6A. In FIG. 6B, it can be seen that the device has a spherical surface 66 which is set against the skin and thereby stretches the skin prior to injection. The activation button releases the compressed gas which propels the toroidal needle loaded with drug a certain distance intracutaneously.

Figure 7A:
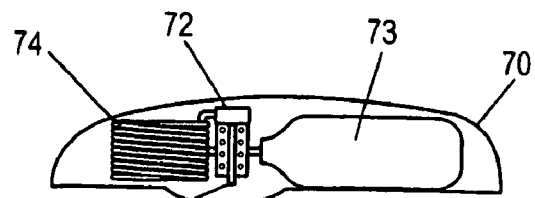
FIGS. 7a-7c depict another embodiment of an injection device, a low-profile gas auto injector, in accordance with the present invention.
Figure 7B:
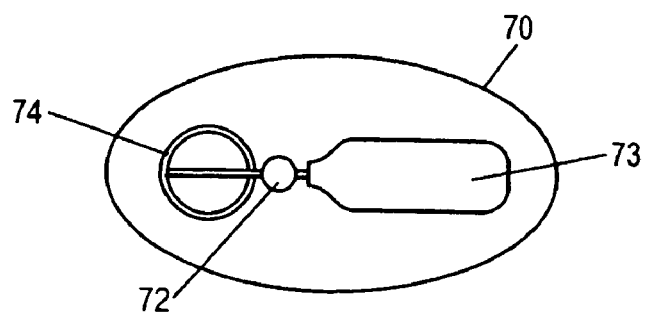
Figure 7C:
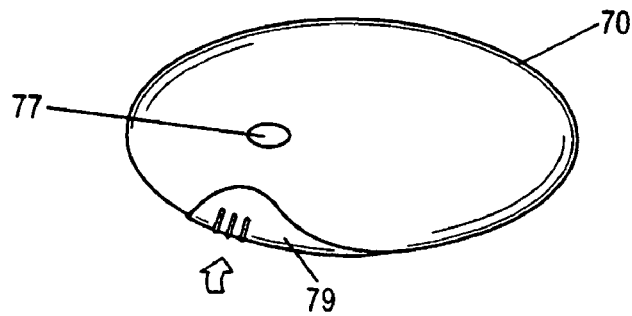

FIGS. 7A-7C depicts another embodiment of an injection device, a low-profile gas auto injector, in accordance with the present invention. FIG. 7A is a side cross-sectional view of the injection device. It has an outer casing 70, valve 72, compressed gas cylinder 73, toroidal needle 74, and needle tip 75. FIG. 7B is a top cross-sectional view of the device depicting the interior of housing 70, showing the arrangement of the compressed gas cylinder 73, the valve 72 and the toroidal syringe 74. FIG. 7C is a top outer view of the embodiment of FIG. 7 showing the casing 70, indicator 77 and an activation button 79.

Figure 8A:
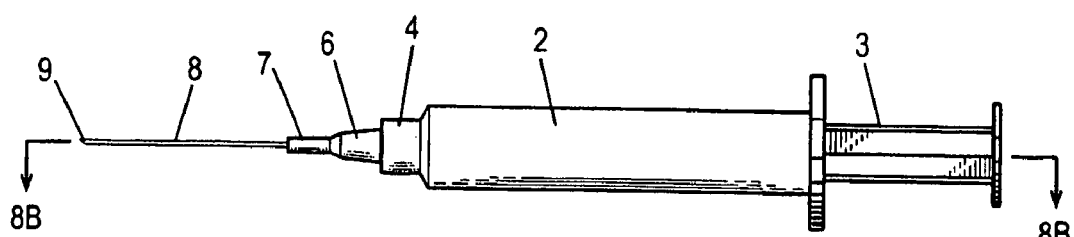
FIGS. 8a-8f are cross sectional views of an injection device and drug formulation filling system in accordance with the present invention.

FIGS. 8A-8F depict a side view of another injection device in accordance with the embodiments of the present invention. FIG. 8A is an outer side view of an injection device (syringe) 1 having a body 2; a plunger 3; a needle hub 4 attached to the proximal end of the body 2 and a needle 5. The needle 5 having a needle tip 6 that fixedly attaches to the needle hub 4; a needle casing 7; needle shaft 8; and a bevel 9. The needle tip 6 attaching inside the needle hub 4. The needle casing 7 is attached to the needle tip 6 and surrounds a piston 10 mechanism (not shown). The needle shaft 8 includes a bevel 9 having an opening at the end distal to the needle tip 6. The bevel 9 opening allows for the outflow of medicament stored in the needle lumen 11 upon activation of the injection device 1.

Figure 8B:
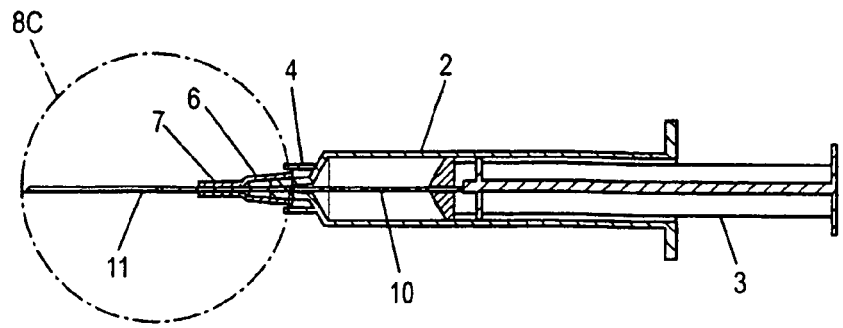

FIG. 8B shows a cross-sectional side view of the administration syringe of FIG. 8A. In particular, FIG. 8B shows the piston 10 and the relationship of the plunger 3 and the needle lumen 8 to the piston 10. The piston 10 is contained within the needle lumen 8 and its length extends from the proximal end of the plunger 3 through the needle tip 6 and needle casing 7 and ends at the needle lumen (drug compartment) 11 portion of the needle lumen 8.

Figure 8C:
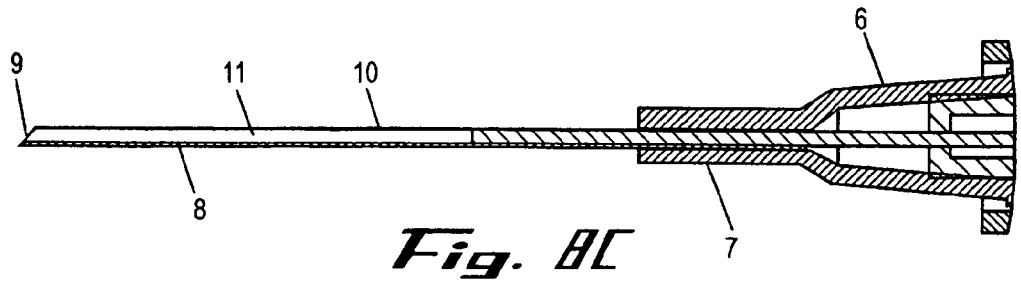

FIG. 8C is a magnified cross-sectional view of the needle 5 of FIG. 8B. FIG. 8B further shows the relationship of the piston 10 and the needle lumen (drug compartment) 11 of the needle shaft 8. FIG. 8C further shows a magnified view of the bevel 9, the needle casing 7 and the needle tip 6.

Figure 8D:
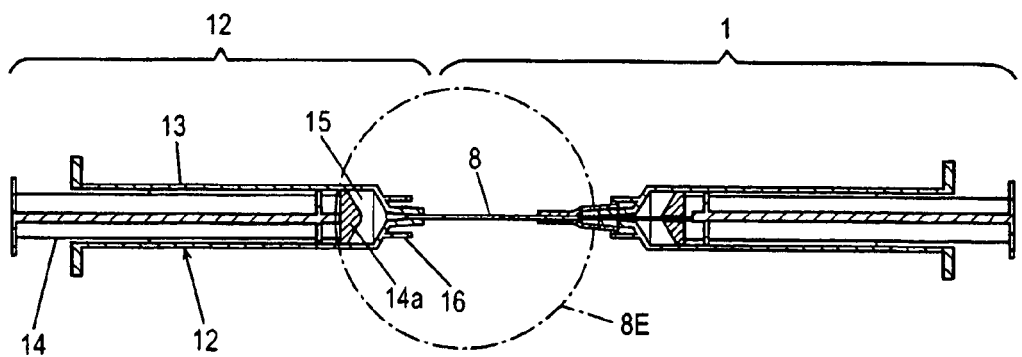

FIG. 8D is a side view of the injection device (syringe) 1 of FIGS. 8A-8C in relationship to a filling device (syringe) 12 for drawing-up a dose(s) of the formulation according to the present invention. In particular, FIG. 8D shows the filling syringe 12 having a body 13, a plunger 14, a stopper 14a, a drug compartment 15 and a needle hub 16. The bevel 9 and a portion of the needle shaft 8 of the injection device 1 are shown as inserted into the needle hub 16 of the filling syringe 12.

Figure 8E:
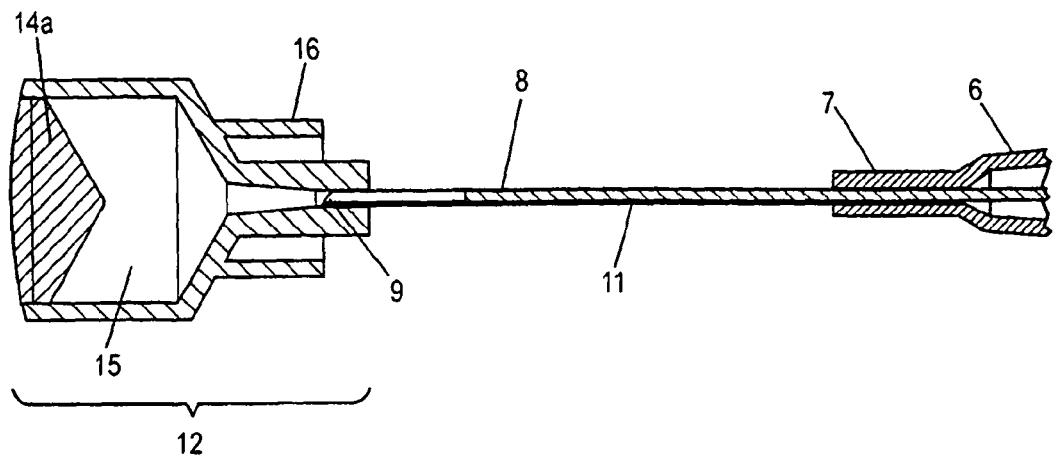

FIG. 8E is a magnified cross-sectional view of FIG. 8D showing the relationship of the needle hub 16 of the filling device 12 and the needle 5 of the injection device 1. The Figure shows the stopper 14a, the drug compartment 15 and the needle hub 16 of the filling device 12, wherein the bevel 9 and a portion of the lumen 11 of the needle 5 from the injection device 1 are inserted into an opening at the end of the needle hub 16 of the filling syringe 12 to allow for the loading of a dose(s) of the formulation of the present invention into the injection device 1.

Figure 8F:
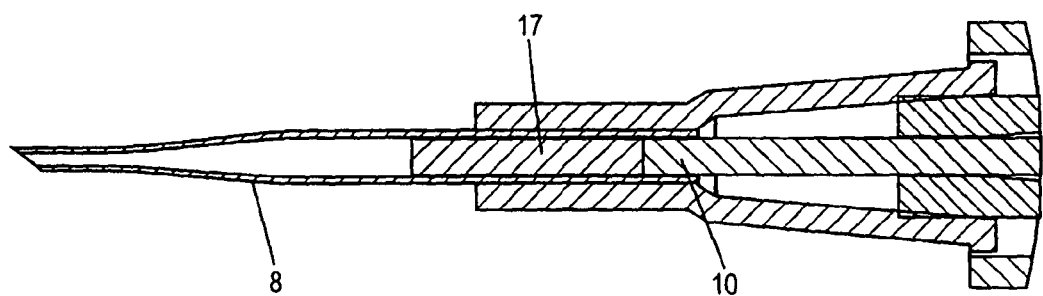

FIG. 8F is a magnified cross-sectional view of the needle 5. FIG. 8F shows a profiled needle shaft 8, the piston 10 and a deformable gel 17 positioned between the needle shaft 8 and the piston 10.

The above-described specific embodiments described in the Figures are illustrative of possible embodiments of the present invention and are not intended to limit the claimed invention in any manner whatsoever. One skilled in the art will appreciate that many other configurations of an injection device utilizing the concepts of the present invention are possible, and such configurations are considered to be encompassed within the appended claims.

The injection device of the invention preferably delivers on the order of a microliter (µl) of solution slurry or paste into the skin. One microliter is one-one thousandth of a cubic centimeter (cc). If the drug slurry and stabilizing solution were of a density of 1.0 g/cc, then 1.0 mg of formulation would be delivered by the invention. Increased doses could be given by either increasing the injection volume, or by increasing the concentration of drug in the formulation slurry.

The thickness of the needle required to avoid a sensation of pain upon administration of the therapeutic drug will depend on the individual patient, formulation and volume of the injection involved. Generally, it is thought that a needle equal to or larger than about 18 gauge (US standard), and more preferably 20 gauge or larger, will suffice. In most practical pain elimination applications, a 27 to 30-gauge needle is required.

For larger volume injections (e.g. monoclonal antibody and sustained-release applications) more sophisticated applicator designs are used that integrate the needle and syringe into a single element to provide smooth, unrestricted flow of the drug paste. These applicators are matched to formulations with specific rheological properties. A narrow, elongated design of the drug chamber is preferred in order to completely deliver the drug formulation slurry into the patient. It is preferred that substantially all, e.g., approaching or equal to 100% volumetric displacement of the formulation is injected into the patient. A deformable gel or rubber tipped piston is used to deliver 100% of the formulation through the profiled needle.

The length of the beveled edge of the needles used in the injection devices of the present invention are from about 0.1 mm to about 1 mm, preferably from about 0.2 to about 0.5 mm. The total length of the needle is preferably from about 1 mm to about 1 cm, most preferably from about 2 mm to about 5 mm.

The amount of solution, slurry or paste delivered into the skin is about a microliter which is the equivalent of one $1/1000^{th}$ of a cubic centimeter. If the drug slurry possesses a density of 1.0 g/cc, then 1.0 mg of formulation would be delivered by the injection. By increasing the injection volume or increasing the concentration of drug in the formulation slurry, increased doses may be administered intracutaneously via the present invention.

In preferred embodiments of the invention, the stabilizing disk generally surrounds the needle and prevents the needle from injecting beyond the dermis and into the subcutaneous regions. Preferably, the distance between the forward end of the needle and the stabilizing disk in contact with the skin surface is tightly controlled to allow a shallow pain-free injection. Upon pressing the activation button the needle is again tightly controlled to penetrate no further than the typical dermal layer of an animal. The depth of penetration of the needle into the skin is limited to preferably from approximately 100 μm to approximately 500 μm, and most preferably around 500 μm+/−0.5 μm, to avoid entry into the subcutaneous layer.

FORMULATION EXAMPLES

Example 1

A dry powder formulation of recombinant human growth hormone was prepared by lyophilizing a 5 mg/ml solution of hGH in 5 mM Tris buffer pH=7.6. Pastes of approximately 30% (w/w) solids were formulated by addition of approximately 230 mg of either N-methy-pyrollidone or an NMP/benzyl benzoate mixture to 100 mg of hGH/Tris to produce a 29% (w/w) hGH formulation. Dissolution of the formulation demonstrates that the NMP/BB mixture resulted in greater recovery of soluble hGH (50% versus 12%). The formulation was then filled into the lumen of a 25 gauge needle using a specially designed filling device such as the device shown in FIG. 8(d). Approximately 10 mg of recombinant human growth hormone containing formulation were included in the quantity of solid formulation included in the injection device. The filled system was then used to administer the solid formulation intracutaneously into a rat. The full dose was delivered to a shallow depth without noticeable irritation of the skin.

Example 2

Another formulation would be formulating human glucagon for dry delivery via the delivery device described herein. The formulation for human glucagon takes place on two steps: First, lyophilized powder development. And second, biocompatible carrier development. Current injectable formulations of glucagon occurs as 1 mg of glucagon in 49 mg of lactose at pH less than 3.0. The formulation envisioned by the present invention provides an efficacious dose of glucagon in a minimal volume using as little stabilizer as possible to stabilize the glucagon during the freeze-drying process as well as during the shelf life. This is achieved by freeze-drying the glucagon at as high a concentration as possible. An example of such a formulation would be 1 mg of glucagon in 3 μl total volume.

All formulations are prepared as aqueous formulations at pH of about 3.0 or lower. Citric acid is used to adjust the pH, however, those of skill in the art would know of alternatives. Sucrose is added as a stabilizer as it is preferred to the reducing sugar lactose. Examples of glucagon/stabilizer ratios would be glucagon:sucrose of 1 to 0.5, or 1 to 1. It is also possible to use glucagon:sucrose:tween in the ratio of 1 to 1 to 0.01. The fluid carrier is a biocompatible non-solvent of proper proportion chosen from, for example, benzyl benzoate, N-methylpyrrolidone, or glycerin.

The invention has been described in an illustrative manner, and it is to be understood that the particular embodiments depicted in the figures and the terminology which has been used has been intended in a nature of words of description rather then of limitation. It is to be further understood that any combination of the ingredients/therapeutic agents described in the foregoing paragraphs are deemed to be encompassed by the appended claims. It is to be further understood that all specific embodiments of the injection device are deemed to be encompassed by the appended claims. Many modifications and variations of the present invention are possible in light of the above teachings. It is therefore to be understood that the obvious modifications are deemed to be encompass within the appended claims.

What is claimed is:

1. A composition for intracutaneous injection of a therapeutic agent, said composition comprising about 0.1 to about 10 microliters of an ultraconcentrated semisolid, said ultraconcentrated semisolid comprising an effective amount of said therapeutic agent homogeneously contained within a pharmaceutically acceptable carrier, wherein said ultraconcentrated semisolid comprises from about 20 to about 85% solids by weight and is in the form of a paste suitable for intracutaneous injection.

2. The composition of claim 1, wherein said therapeutic agent has a mean particle size ranging from 10 nanometers (0.01 microns) to about 100 microns, with no particles being larger than about 500 microns.

3. The composition of claim 1, wherein said therapeutic agent has a mean particle size ranging from about 0.1 microns to about 25 microns, with no particles being larger than about 50 microns.

4. The composition of claim 1, wherein said therapeutic agent has a mean particle size ranging from about 1 to about 10 microns.

5. The composition of claim 1, wherein said ultraconcentrated semisolid further comprises a polymer that imparts thixotropic properties to said composition.

6. The composition of claim 1, wherein said ultraconcentrated semisolid comprises from about 50% to about 80% solids by weight.

7. The composition of claim 1, further comprising an effective amount of a stabilizing agent.

8. The composition of claim 7, wherein said stabilizing agent is a member selected from the group consisting of surfactants, poloxamers, polyols, gels, amphoteric compounds, and mixtures thereof.

9. The composition of claim 1, wherein said composition is stable against unacceptable levels of aggregation, oxidation and hydrolysis related degradation pathways for at least about 2 months when said composition is stored at an elevated temperature of 37° C.

10. The composition of claim 1, wherein said pharmaceutically acceptable carrier is a non-aqueous or semi-aqueous carrier.

11. The composition of claim 1, wherein said pharmaceutically acceptable carrier is a non-aqueous carrier.

12. The composition of claim 1, wherein said pharmaceutically acceptable carrier is selected from the group consisting of alkyl benzoates, aryl benzoates, aralkyl benzoates, triacetin, dimethyl sulfoxide (DMSO), N-methyl-2-pyrrolidone (NMP), and mixtures thereof.

13. The composition of claim 1, wherein said pharmaceutically acceptable carrier is selected from the group consisting of triacetin, N-methyl-2-pyrrolidone (NMP) and benzyl benzoate.

14. The composition of claim 1, wherein said therapeutic agent is subjected to lyophilization, spray-drying or freeze-drying prior to incorporation into said pharmaceutically acceptable carrier.

15. The composition of claim 1, wherein said ultraconcentrated semisolid further comprises a pharmaceutically acceptable polymer in an amount effective to slow the release of said therapeutic agent from said composition upon intracutaneous injection.

16. The composition of claim 1, wherein said therapeutic agent is incorporated into liposomes or conjugated to or incorporated with polysaccharides and/or other polymers to provide a controlled release of said therapeutic agent from said formulation upon intracutaneous injection.

17. The composition of claim 1, wherein said therapeutic agent is a protein, a peptide or a polypeptide.

18. The composition of claim 17, wherein said therapeutic agent is a peptide.

19. The composition of claim 18, wherein said peptide is glucagon.

* * * * *